US010337055B2

(12) United States Patent
Lim et al.

(10) Patent No.: US 10,337,055 B2
(45) Date of Patent: Jul. 2, 2019

(54) METHOD FOR ANALYZING SNPS OF MITOCHONDRIAL DNA USING PNA PROBES AND MELTING CURVE ANALYSIS

(71) Applicant: Republic of Korea (Nat'l Forensic Service Dir., Ministry of Public Admin. and Security), Seoul (KR)

(72) Inventors: Si-Keun Lim, Gangwon-do (KR); Kyungmyung Lee, Gangwon-do (KR); Eu-Ree An, Gangwon-do (KR); Yang-Han Lee, Gangwon-do (KR); Ju Yeon Jung, Gangwon-do (KR); Hyun-Chul Park, Gangwon-do (KR); Ki Won Park, Gangwon-do (KR)

(73) Assignee: REPUBLIC OF KOREA (NATIONAL FORENSIC SERVICE DIRECTOR, MINISTRY OF PUBLIC ADMINISTRATION & SECURITY), Seoul (KR)

( * ) Notice: Subject to any disclaimer, the term of this patent is extended or adjusted under 35 U.S.C. 154(b) by 0 days.

(21) Appl. No.: 15/545,675

(22) PCT Filed: Nov. 17, 2016

(86) PCT No.: PCT/KR2016/013270
§ 371 (c)(1),
(2) Date: Jul. 21, 2017

(87) PCT Pub. No.: WO2018/048021
PCT Pub. Date: Mar. 15, 2018

(65) Prior Publication Data
US 2018/0282793 A1    Oct. 4, 2018

(30) Foreign Application Priority Data

Sep. 12, 2016    (KR) .................. 10-2016-0117459

(51) Int. Cl.
*C12Q 1/6818*    (2018.01)
*C12Q 1/6827*    (2018.01)
(Continued)

(52) U.S. Cl.
CPC ......... *C12Q 1/6832* (2013.01); *C12Q 1/6816* (2013.01); *C12Q 1/6818* (2013.01);
(Continued)

(58) Field of Classification Search
None
See application file for complete search history.

(56) References Cited

FOREIGN PATENT DOCUMENTS

| KR | 10-2008-0022807 A | 3/2008 |
| KR | 10-2014-0046688 A | 4/2014 |

(Continued)

OTHER PUBLICATIONS

Kline, M.C. et al. Journal of Forensic Science 50(2):1 (Mar. 2005).*
(Continued)

*Primary Examiner* — Diana B Johannsen
(74) *Attorney, Agent, or Firm* — Hultquist, PLLC; Steven J. Hultquist

(57) ABSTRACT

A method is disclosed for analyzing single nucleotide polymorphisms (SNPs) of mitochondrial DNA (mtDNA) using a peptide nucleic acid (PNA) probe and a melting curve analysis, and more particularly, a method is disclosed for analyzing SNPs of mtDNA by the melting curve analysis of a PNA probe and mtDNA, in which the PNA probe is coupled with a reporter and a quencher. By using PNA probes labeled with a reporter and a quencher in the method for analyzing SNPs of mtDNA, the time and cost required for individual identification can be drastically decreased, initial analysis can be carried out in the event of a large number of inspections or mass casualties, and human identification information can be coded, and thus the method is very easy to manage and supervise.

9 Claims, 39 Drawing Sheets
(39 of 39 Drawing Sheet(s) Filed in Color)
Specification includes a Sequence Listing.

(51) Int. Cl.
*C12Q 1/6876* (2018.01)
*C12Q 1/6832* (2018.01)
*C12Q 1/6816* (2018.01)
*C07K 14/00* (2006.01)

(52) U.S. Cl.
CPC ......... *C12Q 1/6827* (2013.01); *C12Q 1/6876* (2013.01); *C07K 14/003* (2013.01)

(56) References Cited

FOREIGN PATENT DOCUMENTS

| | | |
|---|---|---|
| KR | 1020150028063 A | 3/2015 |
| KR | 10-2015-0136558 A | 12/2015 |
| WO | 2012075230 A1 | 6/2012 |

OTHER PUBLICATIONS

Ross, P.L. Analytical Chemistry 69(20):4197 (Oct. 1997).*
Nov. 14, 2016 Office Action issued in Korean Patent Application No. 10-2016-0117459.
English Translation of the Nov. 14, 2016 Office Action issued in Korean Patent Application No. 10-2016-0117459.
Mar. 16, 2017 Notice of Allowance issued in Korean Patent Application No. 10-2016-0117459.
English Translation of the Mar. 16, 2017 Notice of Allowance issued in Korean Patent Application No. 10-2016-0117459.
Edited by Sambrook, J., et al., "Protocols 1-5", "Molecular Cloning: A Laboratory Manual—vol. 1", 2001, pp. 1.1-1.5, Publisher: Cold Spring Harbor Press.

* cited by examiner

HV 1 A SET

HV 1-P16311-9

HV 1-P16129

HV 1-P16172

HV 1-P16217-23

HV 1 B SET

HV 1-P16182-3-9

HV 1-P16362

HV 2 A SET
HV 2-P146-50-52

HV 1 A SET

HV 1 B SET

HV 2 B&C SET

HV 1 A SET

HV 1-P16311-9

HV 1-P16129

HV 1-P16172

HV 1-P16217-23

HV 1-P16278

HV 1 B SET

HV 1-P16182-3-9

HV 1-P16362

HV 1-P16261

HV 2 A SET

HV 2-P146-50-52

HV 2 B SET

HV 2-P195-9

HV 2 C SET

FIG. 4

FIG. 5 mtDNA HV 1 / HV 2 T_m reference code

METHOD FOR ANALYZING SNPS OF MITOCHONDRIAL DNA USING PNA PROBES AND MELTING CURVE ANALYSIS

CROSS-REFERENCE TO RELATED APPLICATIONS

This application is a U.S. national phase under the provisions of 35 U.S.C. § 371 of International Patent Application No. PCT/KR2016/013270 filed Nov. 17, 2016, which in turn claims priority of Korean Patent Application No. 10-2016-0117459 filed Sep. 12, 2016. The disclosures of such international patent application and Korean priority patent application are hereby incorporated herein by reference in their respective entireties, for all purposes.

BACKGROUND

Field

The present invention relates to a method for analyzing single nucleotide polymorphism (hereinafter, simply referring to as "SNP") of mitochondrial DNA using a peptide nucleic acid (hereinafter, simply referring to as "PNA") probe and a melting curve analysis and more particularly, to a method for analyzing SNP of mitochondrial DNA by analyzing a melting curve of a PNA probe and mitochondrial DNA using the PNA probe coupled with a reporter and a quencher.

Description of the Related Art

Mitochondrial DNA (mtDNA), widely used in phylogenetic studies for the tracing of maternal lineage, has inherited characteristics from mother to her offspring. Such mtDNA is about 16 kb in size and is used for phylogenetic studies by focusing on the control region of about 1.1 kb, which shows a high mutation rate in the individual. Various papers have reported that hypervariable (HV) regions 1 and 2 of the control region are particularly very meaningful regions which can be classified by individual or race.

The control region of mtDNA has been used as a very important identification marker in the forensic field. It is further used as a very important scientific basis in the forensic field all over the world. Currently, the mtDNA analysis is performed using Sanger sequencing which is a gold standard. SNP, mutation information on the correct base sequence in the mtDNA control region, can be confirmed by Sanger sequencing analysis. However, there are disadvantages that it takes a lot of time to analyze samples, and both experimenters and researchers have to confirm and check the analysis results one by one for the comparative analysis of the results. Further, nonspecific products may occur during gene amplification, thereby causing adverse effects on the analysis results. Moreover, their analysis equipment is very expensive, and they need specialists for sample analysis.

PNA probes are analyzed by using a hybridization method different from the conventional hydrolysis methods, have excellent ability to identify specific regions or to distinguish markers, and have high specificity reacting only at the complementary base sequence, so the PNA probe has the advantage of solving the problems of the conventional probes. In particular, the PNA probe may be used in a single PNA probe to distinguish base mutations. Therefore, it is possible to perform mutation analysis of various bases using only one PNA probe in genotype analysis. Low-cost devices, e.g., real-time polymerase chain reaction (hereinafter, simply referring to as "real-time PCR") gene amplifiers, are used compared to Sanger sequencing, and thus there is little cost and time investment in fostering specialized skills. Therefore, low-cost equipment may be used for the PNA probe-based mtDNA analysis method, through screening of initial analysis and encoding of SNP information, which is a high throughput analysis that is very cost effective and can quickly and efficiently analyze massive identification and human identification.

Recently, the fluorescence melting curve analysis (hereinafter, simply referring to as "FMCA") was used as a method for analysis of the PNA probe hybridization. FMCA is an analysis that may classify the difference in the binding force between the product and the PNA probe with melting temperature (Tm) after the PCR amplification reaction. The PNA probe is very easy to design unlike other SNP detection probe, and is designed using 9-15 mer sequences. In order to design a probe with a desired Tm value, the Tm value thus may be adjusted based on the length of the PNA probe or by modifying even PNA probe of the same length.

Furthermore, since PNA has better binding force than DNA to have a higher basic Tm value, it can be designed to have a shorter length than that of DNA, so that it is possible to detect near SNPs. The conventional high resolution melting (hereinafter, simply referring to as "HRM") method is required additional analysis programs or detailed temperature shifts because the difference of the Tm value is very low at about 0.5° C., so that HRM method is difficult to analyze when two or more SNPs are presented. On the other hand, the PNA probe is not affected by SNPs other than the probe's base sequence, and thus many base mutations may be analyzed at the same time.

Thus, the present inventors have made efforts to develop an identification method using mtDNA easily and effectively, and as a result, it has been confirmed that individuals can be more effectively identified by encoding results of the fluorescence melting curve analysis between the PNA probe and the mtDNA using the PNA probe, thereby completing the present invention.

SUMMARY

An object of the present invention is to provide a method for analyzing SNP of mitochondrial DNA (mtDNA) by a PNA probe complementarily hybridizing to mtDNA and a melting curve analysis.

Further, another object of the present invention is to provide a kit for analyzing SNP of mtDNA, comprising the PNA probe complementarily hybridizing to mtDNA.

Furthermore, still another object of the present invention is to provide a method for providing information on human identification by encoding melting temperature (Tm) between mtDNA and the PNA probe.

In order to achieve the objects as describe above, the present invention provides a method for analyzing SNP of mtDNA, comprises:

(a) hybridizing mtDNA of an subject's sample with a plurality of PNA probes to which a reporter and a quencher are labeled and to be hybridized with a base sequence of the mtDNA;

(b) obtaining a melting curve by melting the hybridized product while changing the temperature; and (c) confirming base sequence variation through the melting curve analysis.

Moreover, the present invention provides a method for analyzing SNP of mtDNA, of which the PNA probe hybridizes to the hypervariable (HV) 1 or 2 region of mtDNA.

Further, the present invention provides a method for analyzing SNP of mtDNA, in which the PNA probes of SEQ ID NOs 1 to 9, which hybridize to the HV 1 region or of SEQ ID NOs 10 to 16, which hybridize to the HV 2 region.

Furthermore, the present invention provides a method for analyzing SNP of mtDNA, in which the reporter is one or more selected from the group consisting of FAM (6-carboxyfluorescein), Texas red, HEX (2',4',5',7'-tetrachloro-6-carboxy-4,7-dichlorofluorescein), Alexa 680 and Cy5.

Moreover, the present invention provides a method for analyzing SNP of mtDNA, in which the quencher is one or more selected from the group consisting of TAMRA (6-carboxytetramethyl-rhodamine), BHQ1, BHQ2 and Dabcyl.

In order to achieve the objects as describe above, the present invention further provides a kit for analyzing SNP of mtDNA, comprising the PNA probes labeling the reporter and the quencher labeled thereto and hybridizing to a base sequence of mtDNA.

Further, the present invention provides a kit for analyzing SNP of mtDNA, of which the PNA probes hybridize to the hypervariable (HV) 1 or 2 region.

Furthermore, the present invention provides a kit for analyzing SNP of mtDNA, in which the PNA probes of SEQ ID NOs 1 to 9, which hybridize to the HV 1 region or of SEQ ID NOs 10 to 16, which hybridize to the HV 2 region.

Moreover, the present invention provides a kit for analyzing SNP of mtDNA, in which the reporter is one or more selected from the group consisting of FAM (6-carboxyfluorescein), Texas red, HEX (2',4',5',7'-tetrachloro-6-carboxy-4,7-dichlorofluorescein), Alexa 680 and Cy5.

Further, the present invention provides a kit for analyzing SNP of mtDNA, in which the quencher is one or more selected from the group consisting of TAMRA (6-carboxytetramethyl-rhodamine), BHQ1, BHQ2 and Dabcyl.

In order to achieve the objects as describe above, the present invention provides a method for providing information for human identification, comprises:

(a) hybridizing mtDNA of an subject's sample with a plurality of PNA probes to which a reporter and a quencher are labeled and to be hybridized with a base sequence of the mtDNA;

(b) obtaining melting temperature (Tm) of the mtDNA and the PNA probes for each of the PNA probes by melting the hybridized product while changing the temperature; and (c) grouping the Tm obtained for each of the PNA probes to give codes to the probes.

Further, the present invention provides a method for providing information for identification, in which the PNA probes hybridize to the hypervariable (HV) 1 or 2 region of the mtDNA.

Furthermore, the present invention provides a method for providing information for identification, in which the PNA probes of SEQ ID NOs 1 to 9, which hybridize to the HV 1 region or of SEQ ID NOs 10 to 16, which hybridize to the HV 2 region.

Moreover, the present invention provides a method for providing information for identification, in which the reporter is one or more selected from the group consisting of FAM (6-carboxyfluorescein), Texas red, HEX (2',4',5',7'-tetrachloro-6-carboxy-4,7-dichlorofluorescein), Alexa 680 and Cy5.

Further, the present invention provides a method for providing information for identification, in which the quencher is one or more selected from the group consisting of TAMRA (6-carboxytetramethyl-rhodamine), BHQ1, BHQ2 and Dabcyl.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows the encoding for each of probes for 73 samples.

FIG. 5 shows reference melting temperature (Tm) codes of information on mtDNA base sequence.

DETAILED DESCRIPTION OF THE EMBODIMENT

Figure 1:
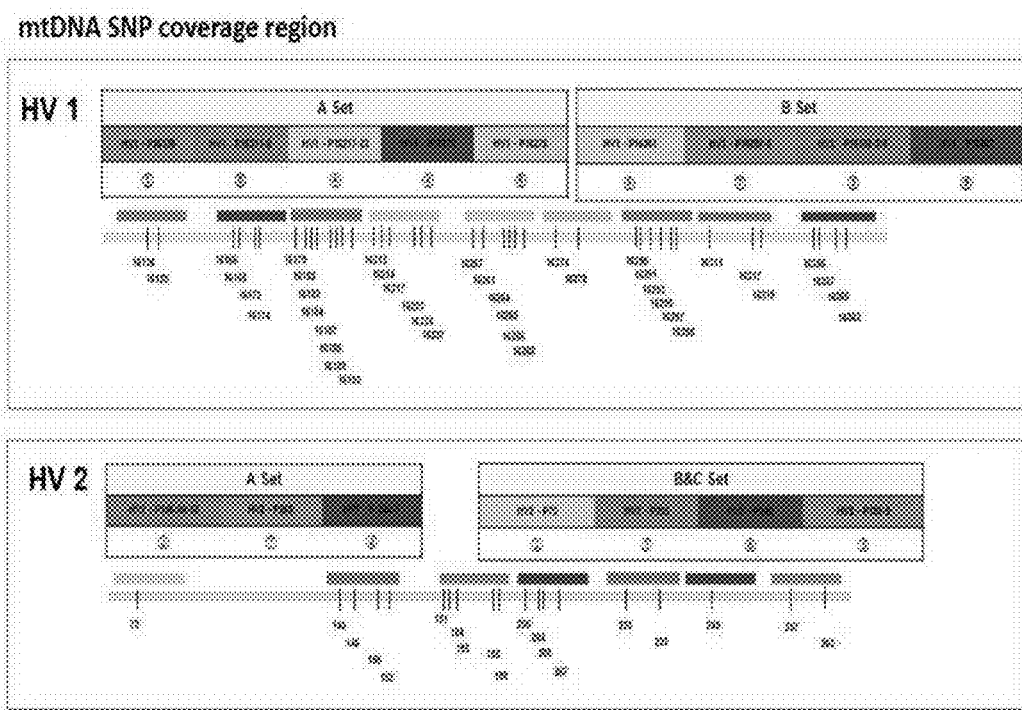
FIG. 1 shows a PNA probe coverage region for analyzing mtDNA genotypes.

Unless otherwise defined, all technical and scientific terms used herein have the same meaning as commonly understood by one of ordinary skill in the art to which the present invention belongs. In general, the nomenclature used herein and the experimental methods described below are well known and commonly used in the art.

As a result of efforts to develop a simple and effective identification method, the present invention has been made to confirm that an object can be more effectively identified by encoding a fluorescence melting curve analysis of a PNA probe and mitochondrial DNA (mtDNA) using the PNA probe.

An aspect of the present invention relates to a method for analyzing SNP of mtDNA, comprises: (a) hybridizing the mtDNA of an subject's sample with a plurality of PNA probes to which a reporter and a quencher are labeled and to be hybridized with a base sequence of the mtDNA; (b) obtaining a melting curve by melting the hybridized product while changing the temperature; and (c) confirming base sequence variation through the melting curve analysis.

"Hybridization" of the present invention means that complementary single-stranded nucleic acids form a double-stranded nucleic acid. Hybridization may occur either in perfect match in complementarity between two nucleic acid strands, or even in the presence of some mismatching bases. The degree of complementarity required for hybridization may vary depending on the hybridization conditions and can be particularly controlled by temperature.

Further, a plurality of melting curves may be obtained for the plurality of PNA probes, and a plurality of melting curves obtained by melting a plurality of hybridized products can be respectively analyzed to confirm the base sequence mutations.

According to another embodiment of the present invention, the plurality of PNA probes may be hybridized with a sample containing mtDNA in one test container. In this case, the PNA probes are preferably designed such that the reporters labeled to the probes are different from each other.

According to the present invention, the melting curve of the PNA probes is analyzed using the base mutation of the mtDNA because the PNA probes have melting temperature (Tm) difference in the SNP. According to one exemplary embodiment of the present invention, 16 PNA probes complementary to the base sequence of hypervariable region (HV) 1 or 2 of mtDNA were prepared (Table 1). The 16 PNA probes were designed to perform complete hybridization based on the HV 1 region and the HV 2 region. In other words, there is an incomplete hybridization due to SNP or base deletion of the HV 1 and HV 2 regions of mtDNA, resulting in a difference in Tm.

Further, the PNA probes of the present invention comprise PNA probes of SEQ ID NOs 1 to 9, which hybridize to the HV 1 region or of SEQ ID NOs 10 to 16, which hybridize to the HV 2 region.

"Base mutation" of the present invention refers to mutation of the base sequence of the mtDNA and comprises SNP as well as mutation caused by base substitutions, deletions, or insertions.

The PNA probes of the present invention for analyzing SNP of the mtDNA containing the reporter and the quencher is hybridized with each mtDNA, and then fluorescence signals are generated. As the temperature increases, they rapidly melt with the mtDNA at a proper Tm of the probe, and thus the fluorescence signals are quenched. SNP of mtDNA can be identified through high resolution fluorescence melting curve analysis (FMCA) obtained from the fluorescence signals according to the temperature shifts.

According to the present invention, fluorescence material of the reporter and the quencher capable of quenching the reporter fluorescence is labeled to each end thereof for the melting curve analysis using the PNA probes.

The reporter may be one or more selected from the group consisting of FAM (6-carboxyfluorescein), Texas red, HEX (2',4',5',7'-tetrachloro-6-carboxy-4,7-dichlorofluorescein), Alexa 680 and Cy5. Further, the quencher may be one or more selected from the group consisting of TAMRA (6-carboxytetramethyl-rhodamine), BHQ1, BHQ2 and Dabcyl, but is not limited thereto, and Dabcyl is preferably used.

Samples including the mitochondrial nucleic acid relate to a tissue or body fluid containing cells from which mtRNA and mtDNA can be obtained. For example, the biological sample may be, but is not limited to, skin, lung, breast, prostate, nerve, muscle, heart, stomach, colon, and rectum tissue, and may be derived from blood, saliva, brain spinal fluid, sputum, urine, mucus, capsular fluid, peritoneal fluid, amniotic fluid, and the like.

The sample containing the mitochondrial nucleic acid is DNA or RNA, and the molecule may be a double-stranded or single-stranded form. When the nucleic acid as the initial material is a double strand, it is preferable to make the two strands into a single strand, or a partial single strand form. Methods known to separate strands include, but are not limited to, heat, alkaline, formamide, urea and glycoxal treatment, enzymatic methods such as helicase action, and binding proteins. For example, the strand separation can be performed by thermal treating at a temperature of 80° C. to 105° C. A general method of treatment as described above is disclosed in Joseph Sambrook et al., Molecular Cloning, 2001.

Figure 2B:
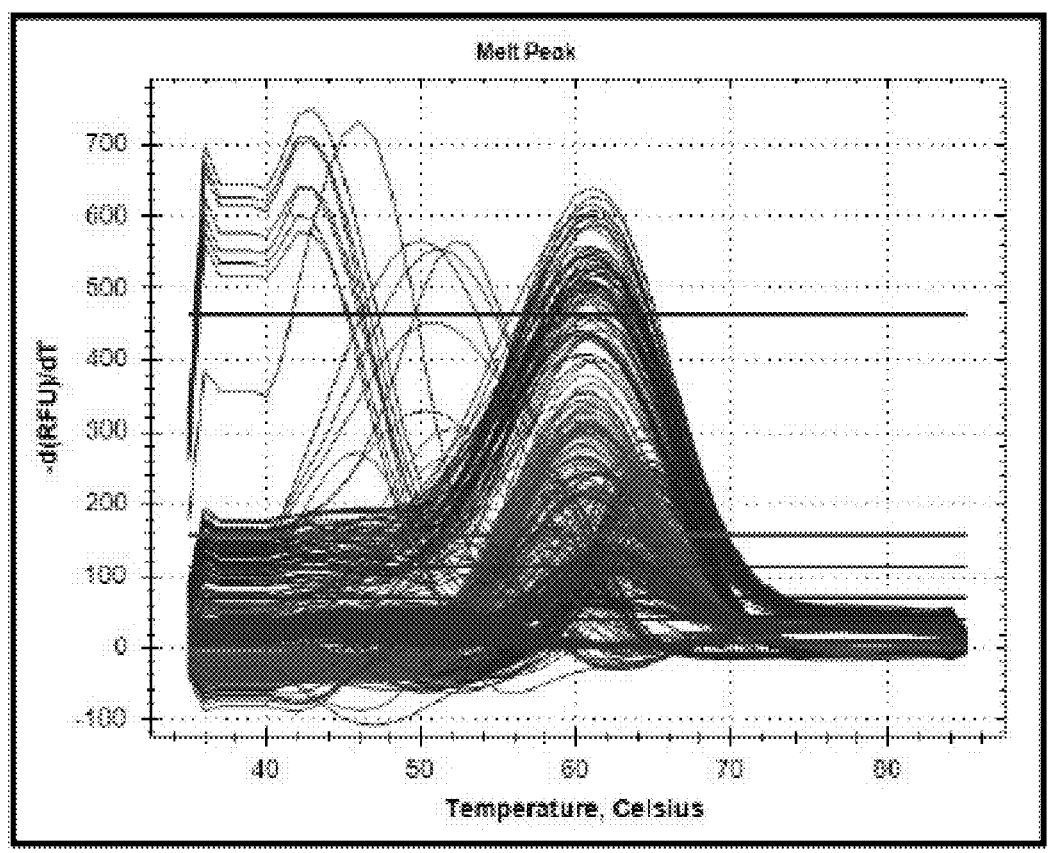
Figure 2B:
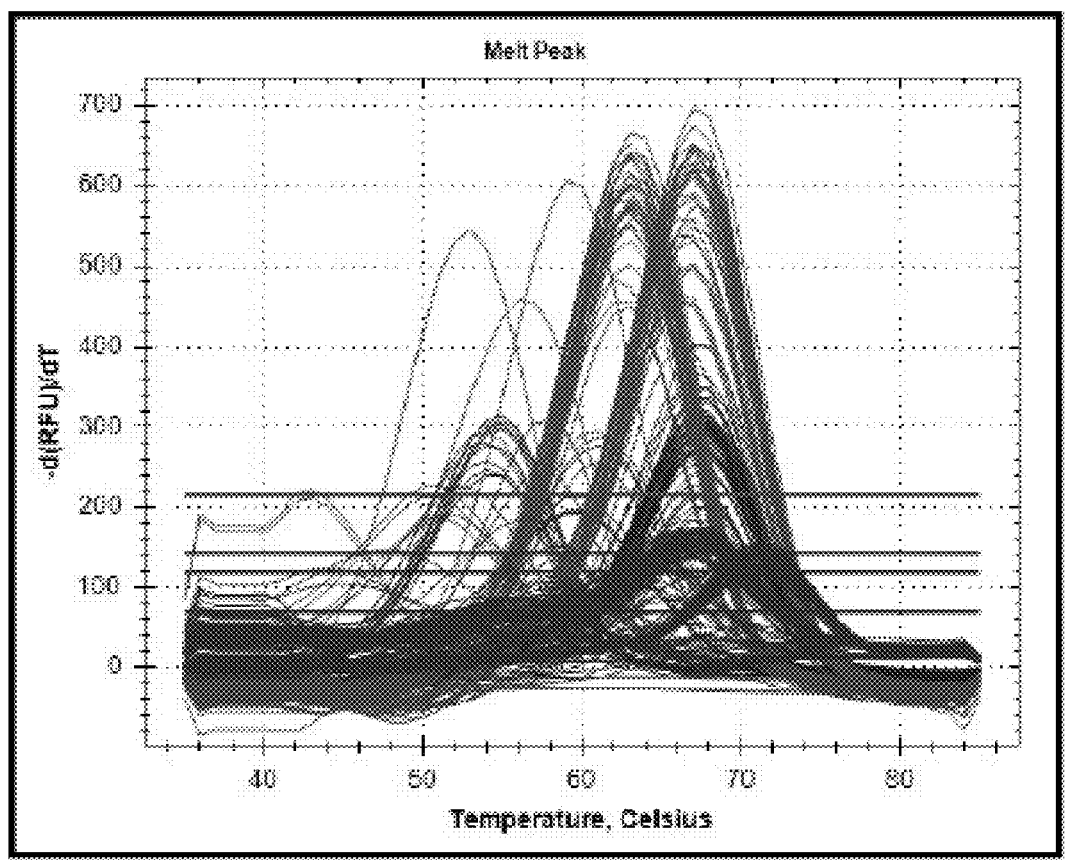
Figure 2B:
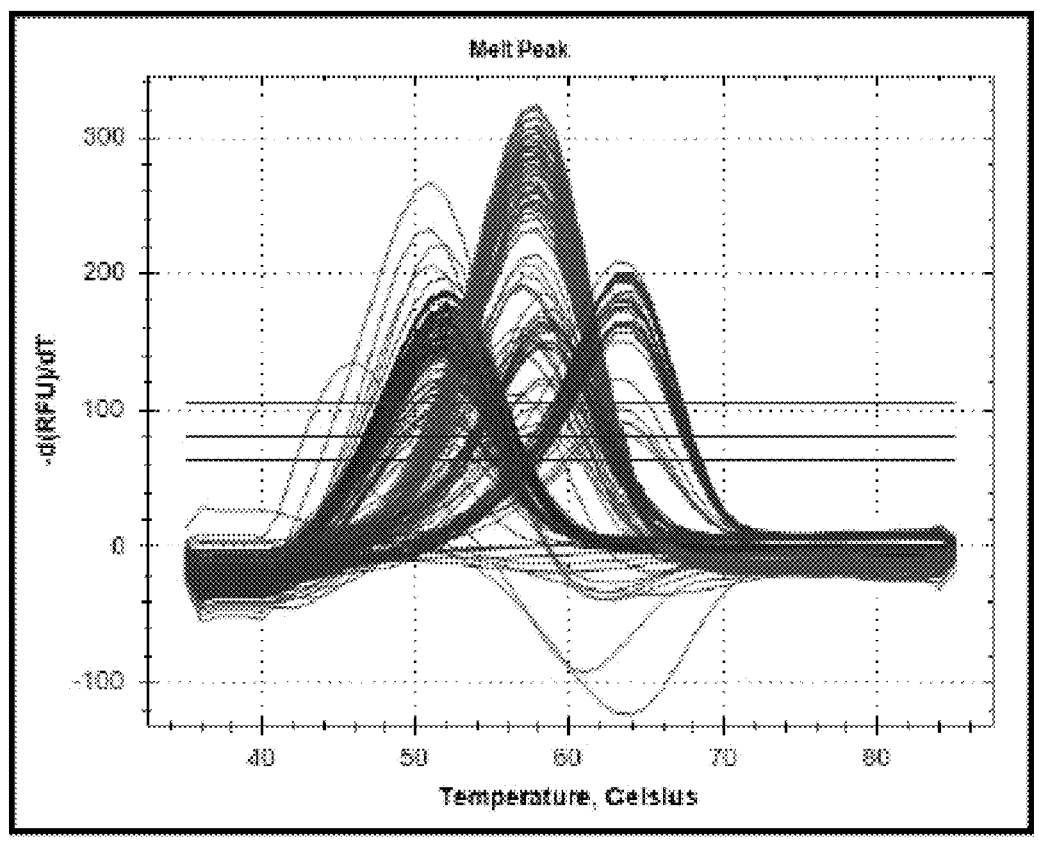
Figure 2B:
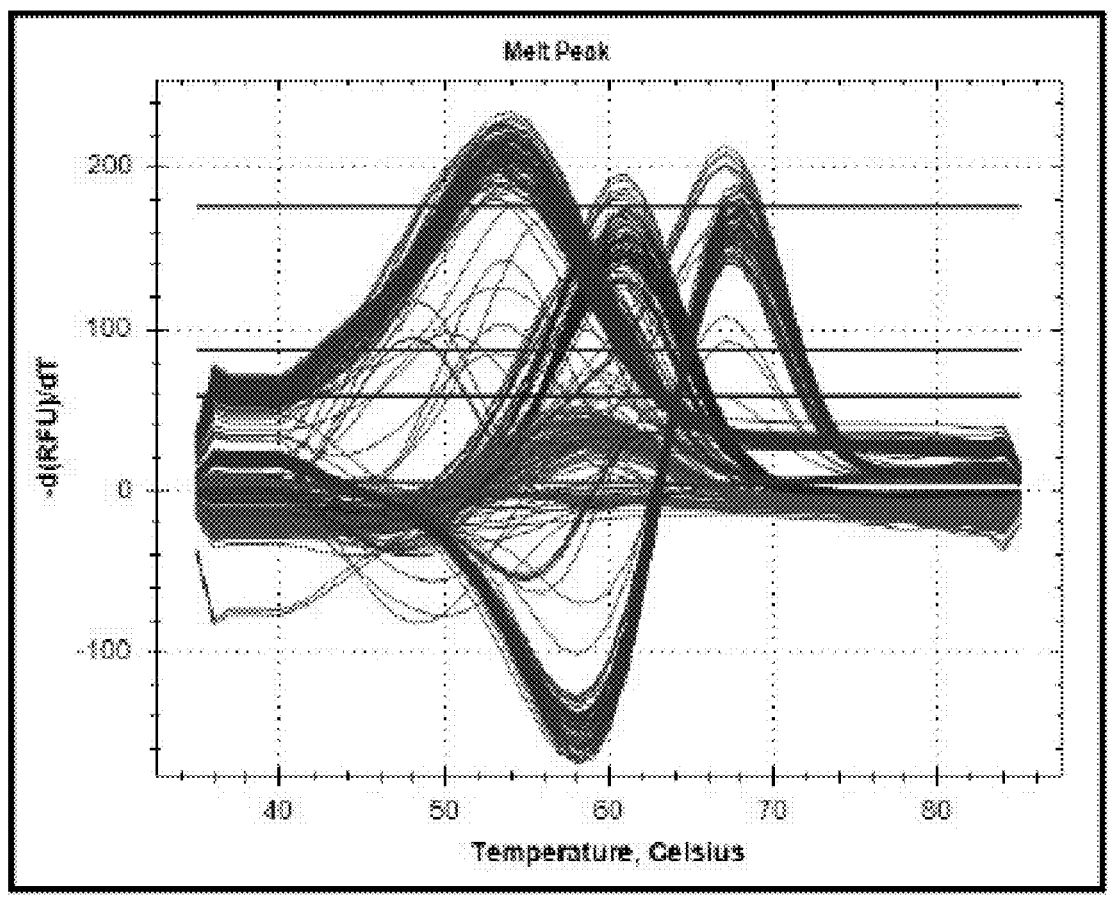
Figure 3:
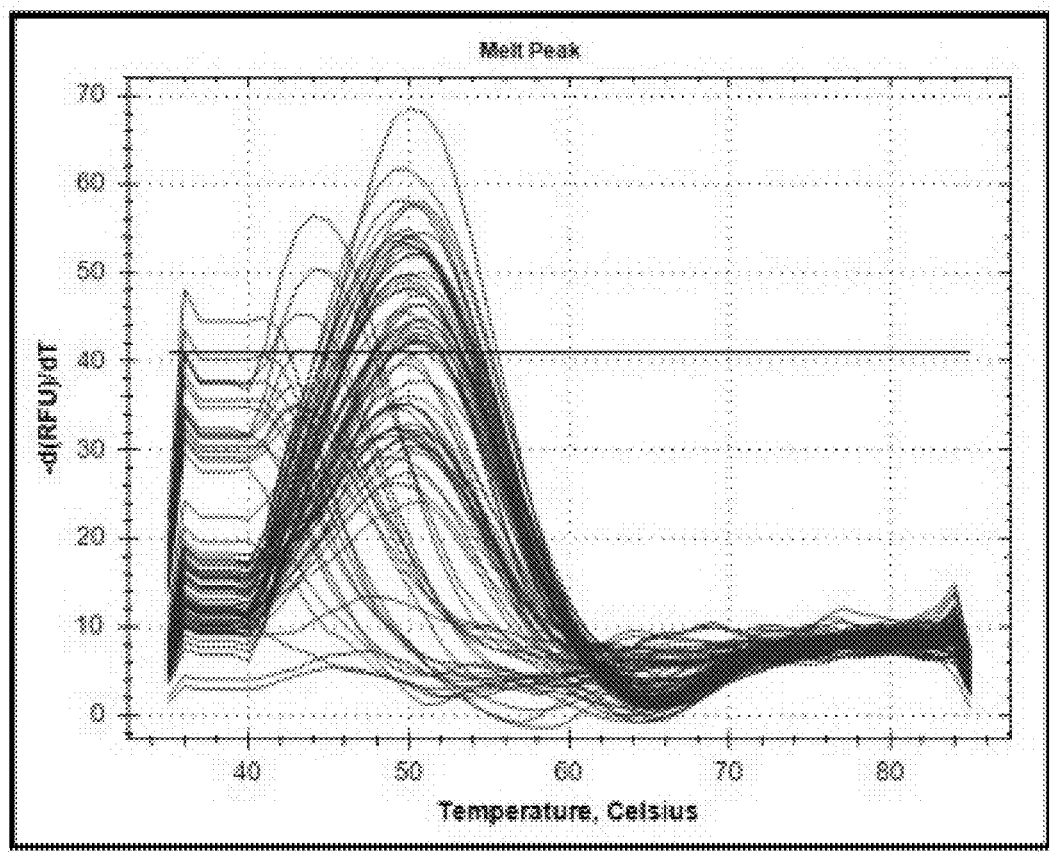
FIG. 3 shows the melting curve analysis for each set and probe of a base sequence analysis of mtDNA for 73 samples.
Figure 3:
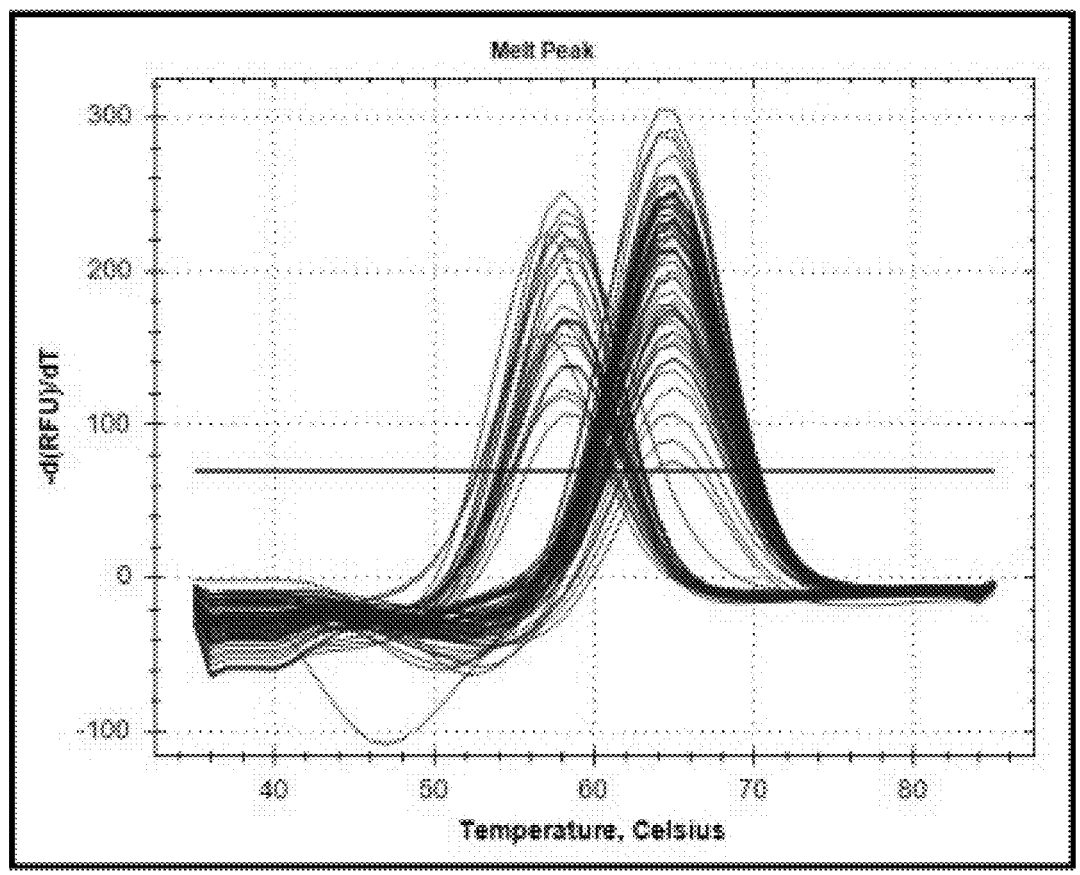
Figure 3:
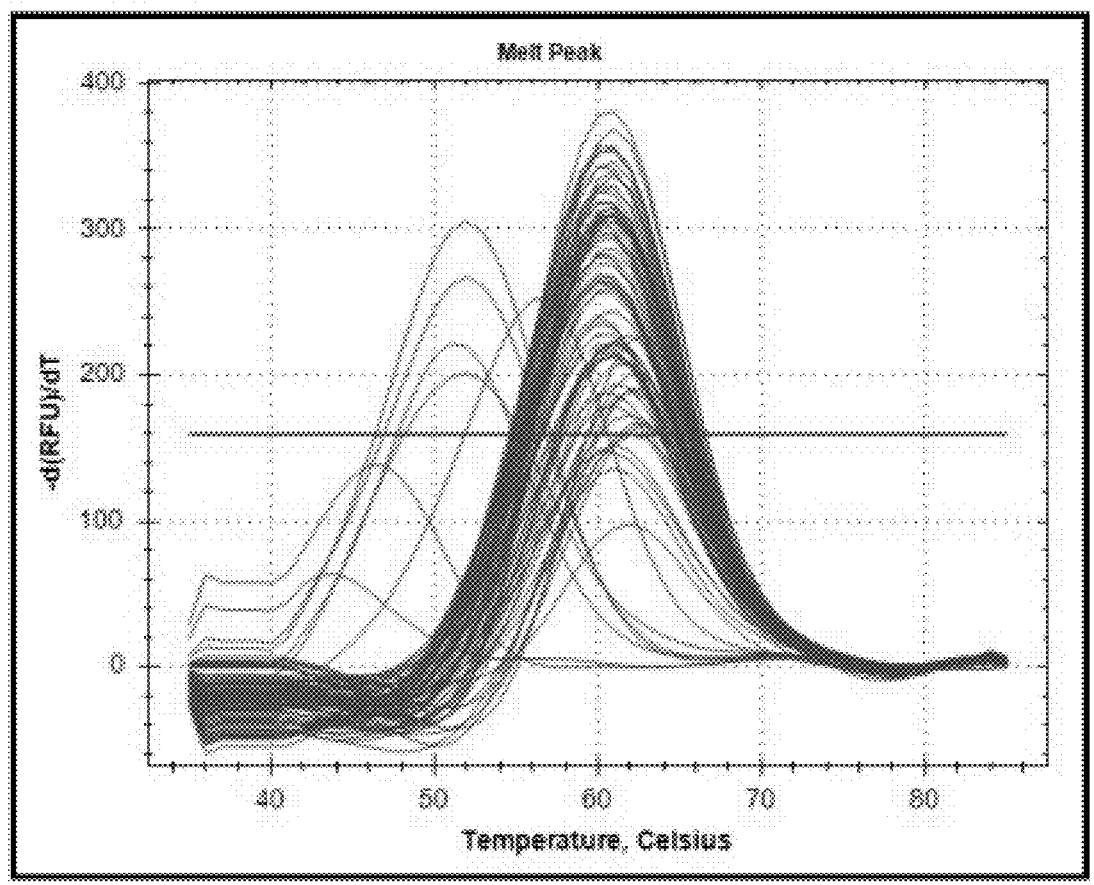
Figure 3:
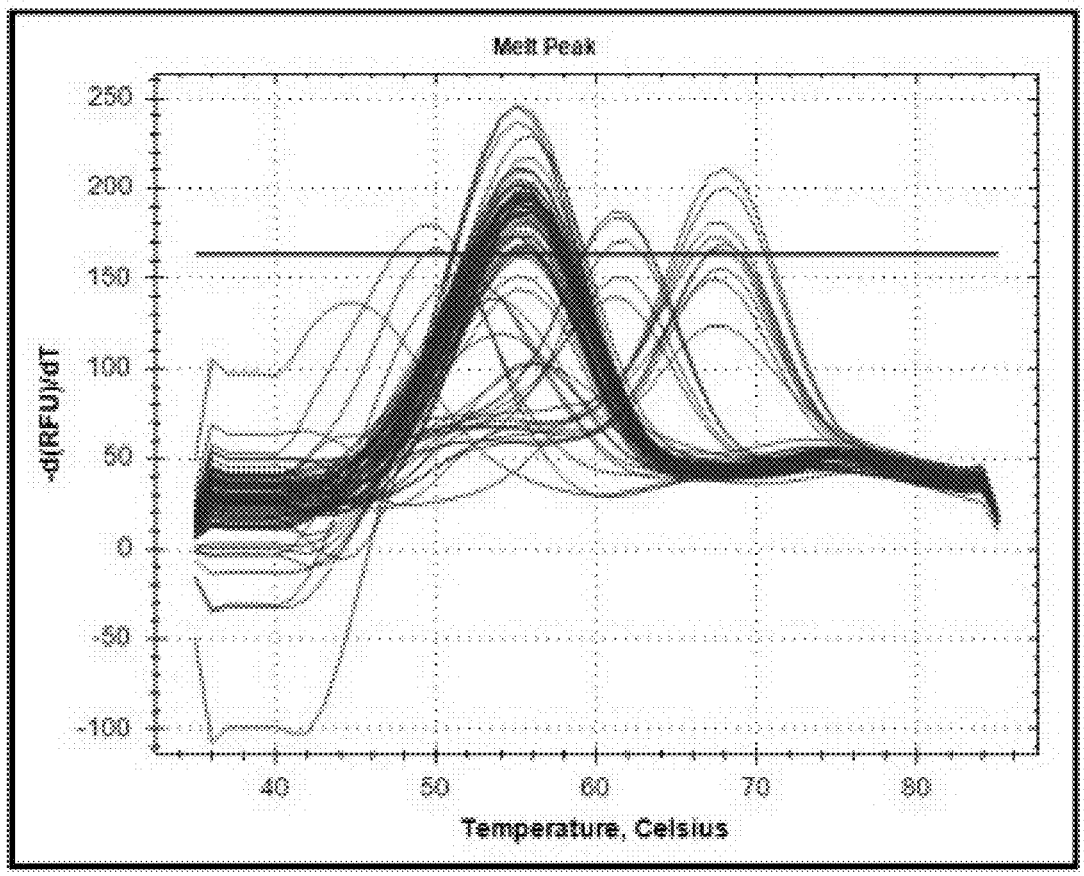
Figure 3:
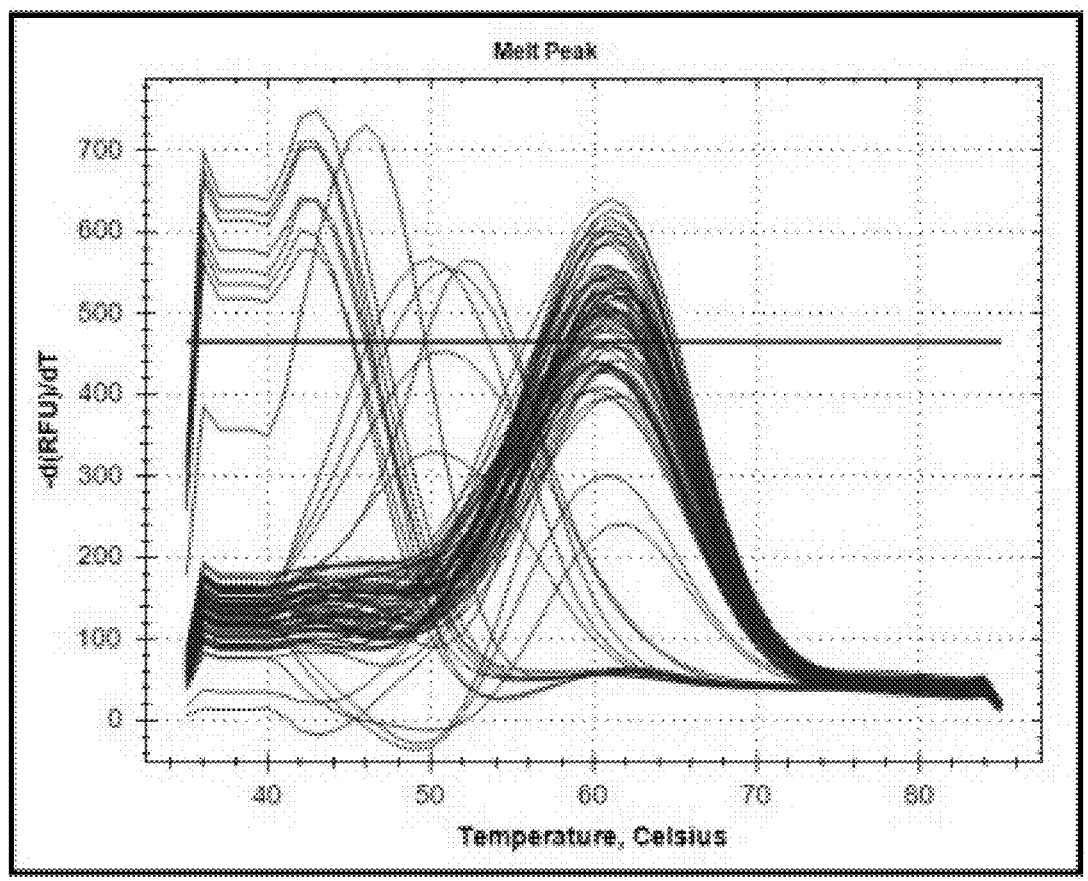
Figure 3:
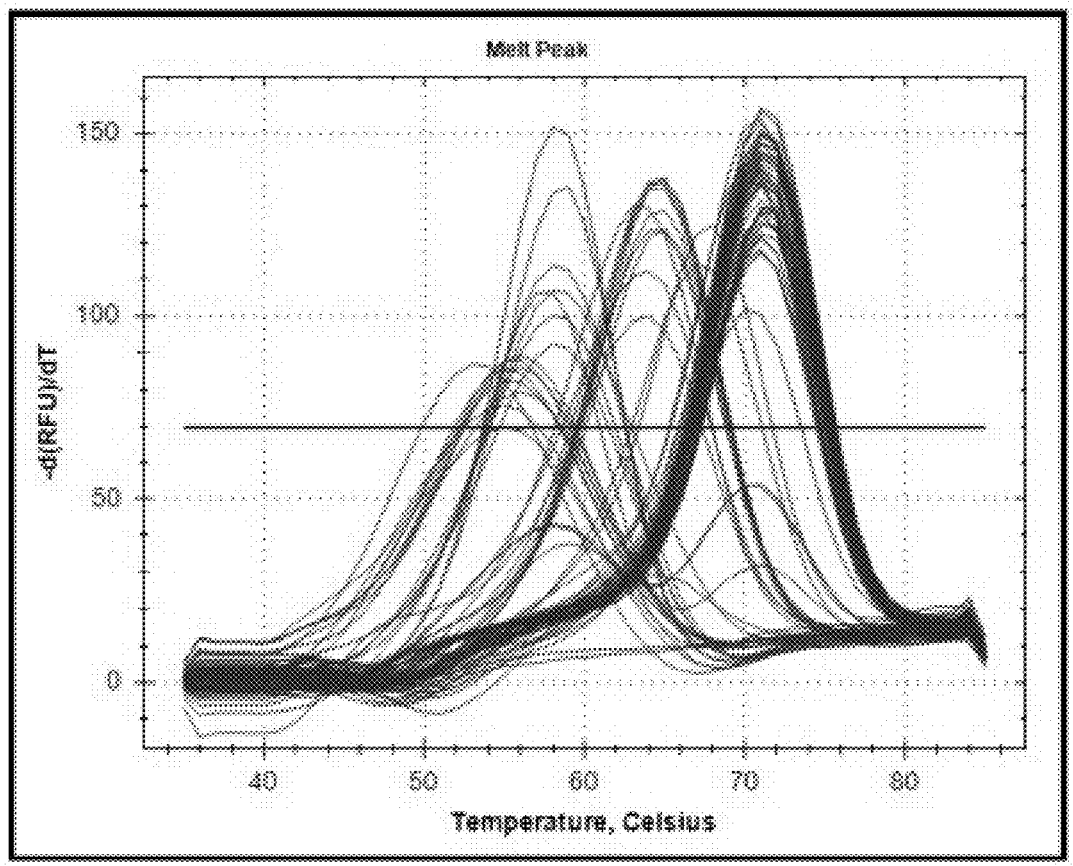
Figure 3:
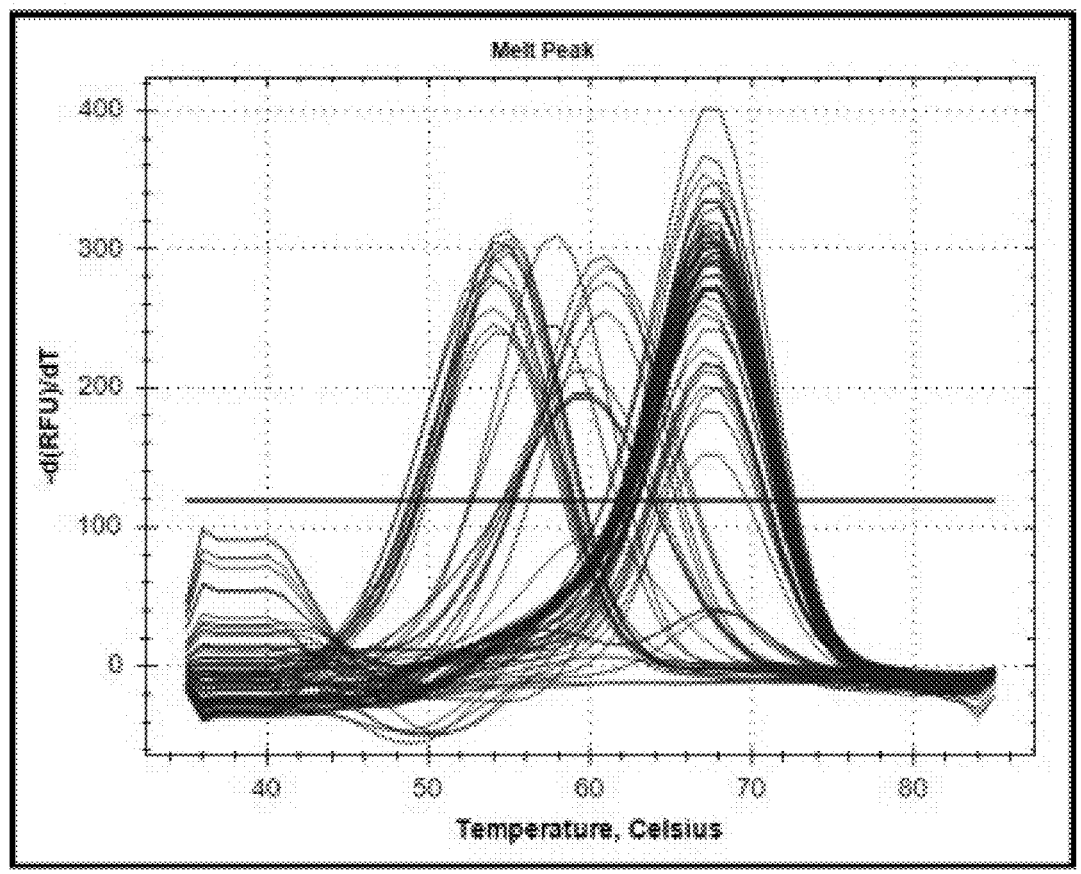
Figure 3:
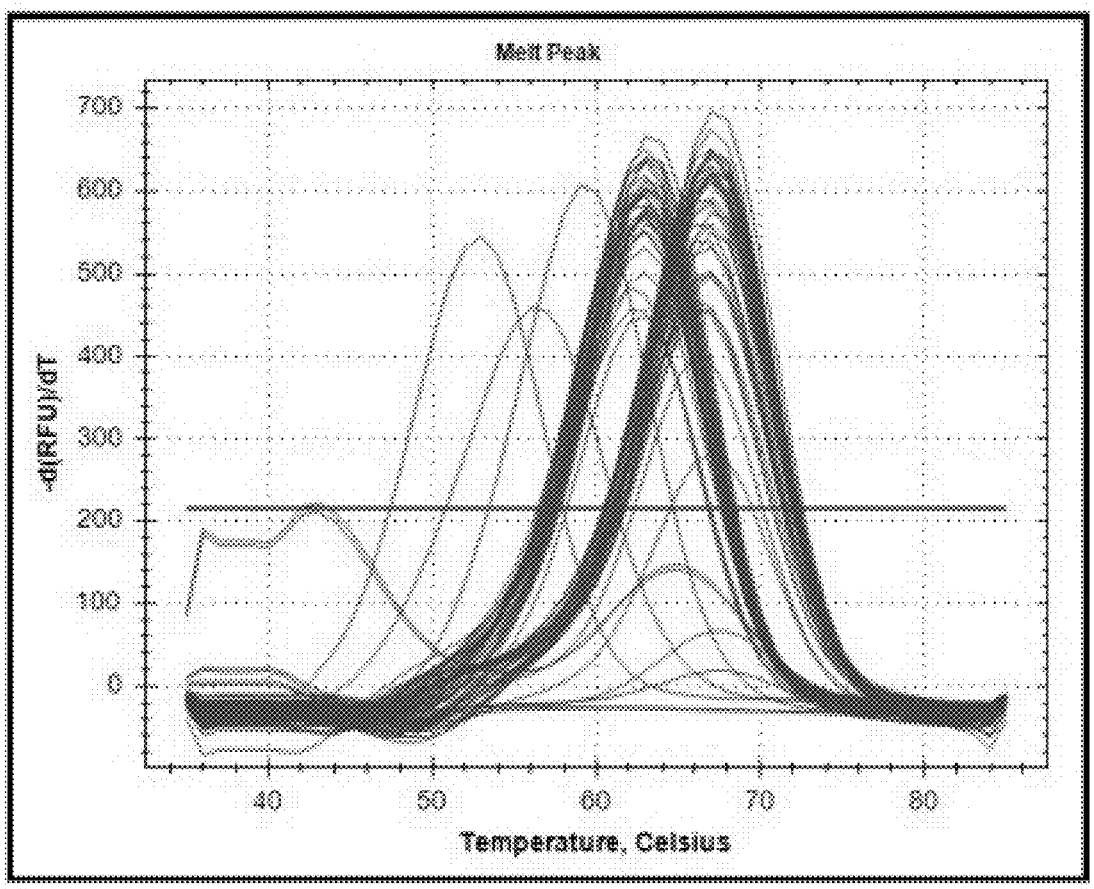
Figure 3:
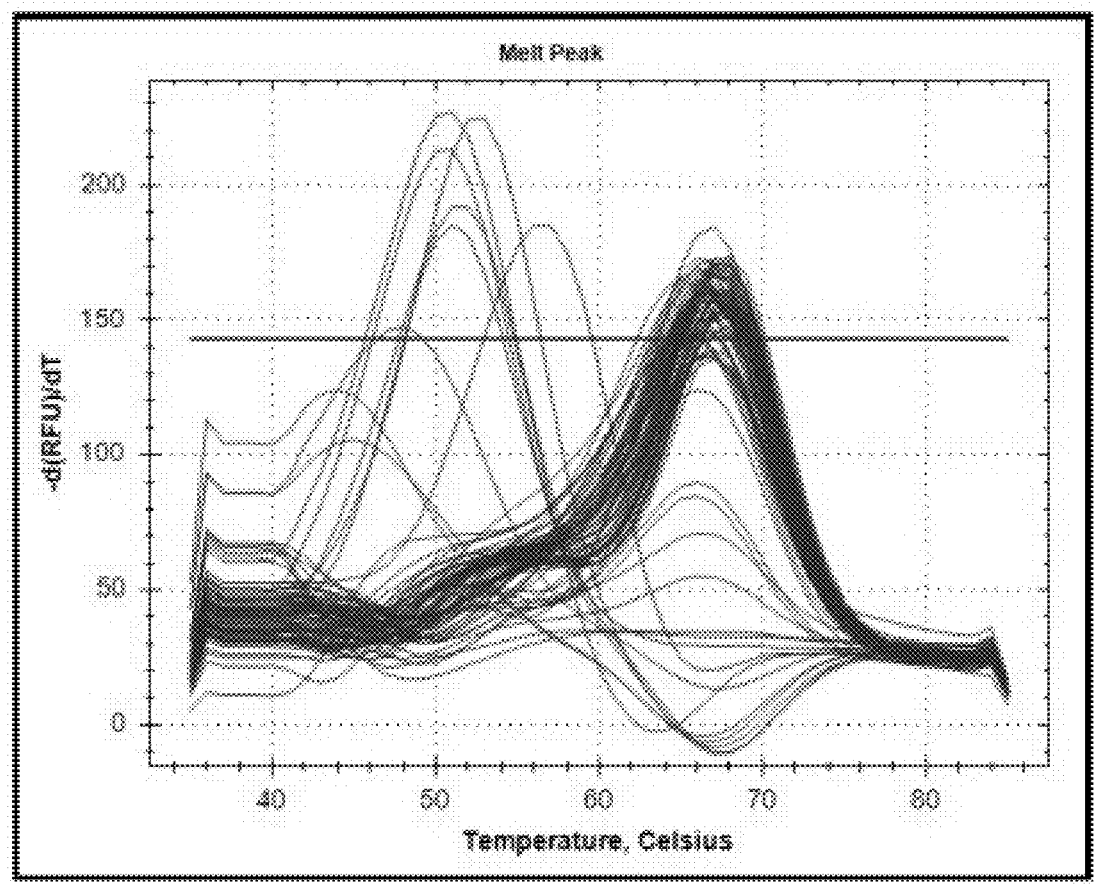
Figure 3:
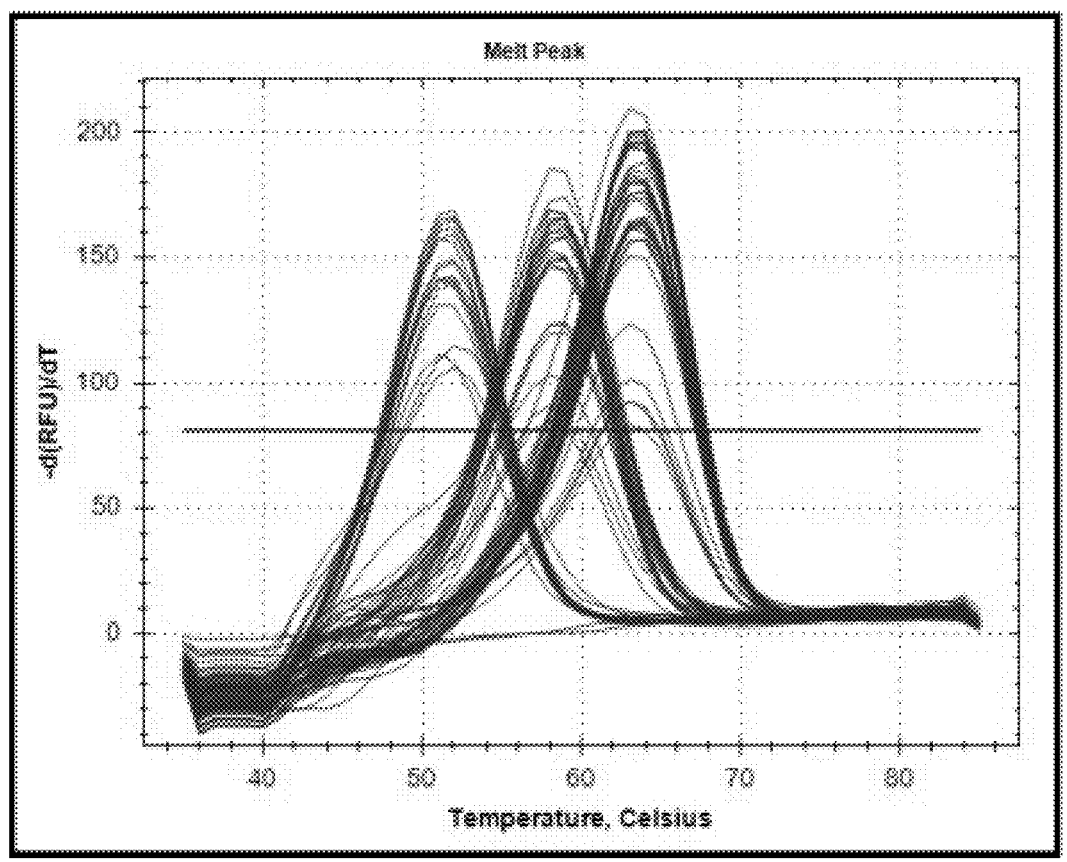
Figure 3:
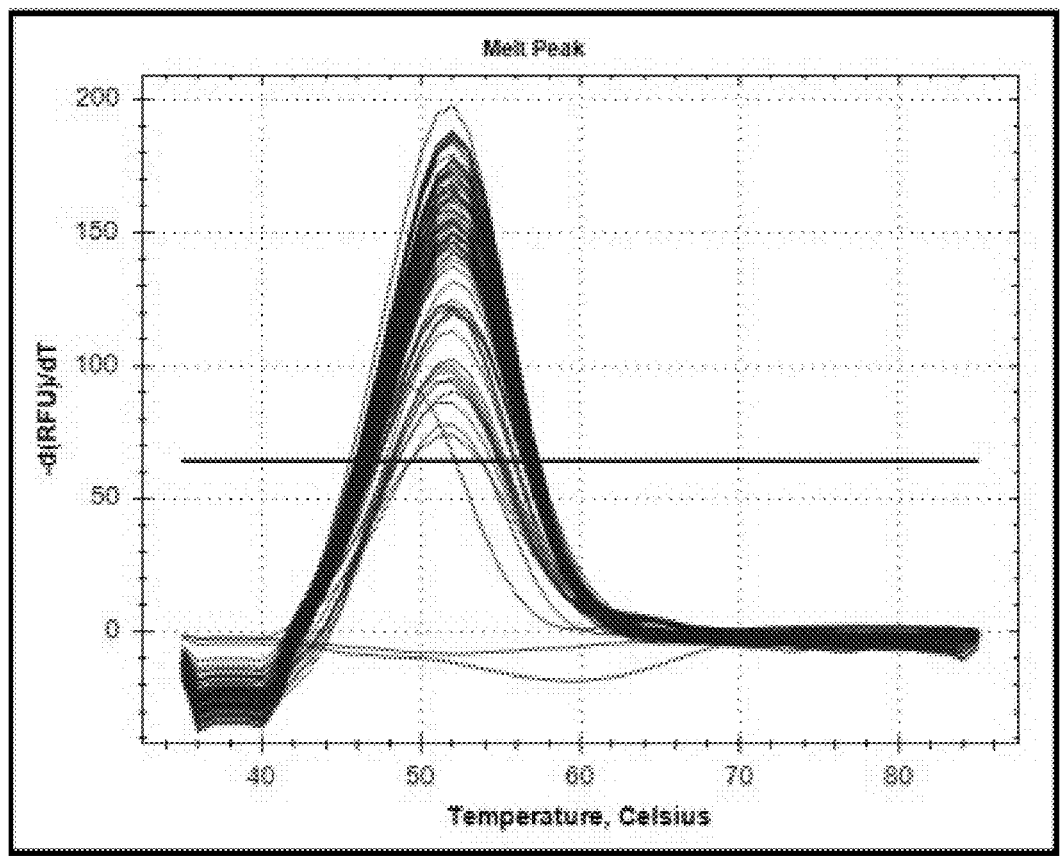
Figure 3:
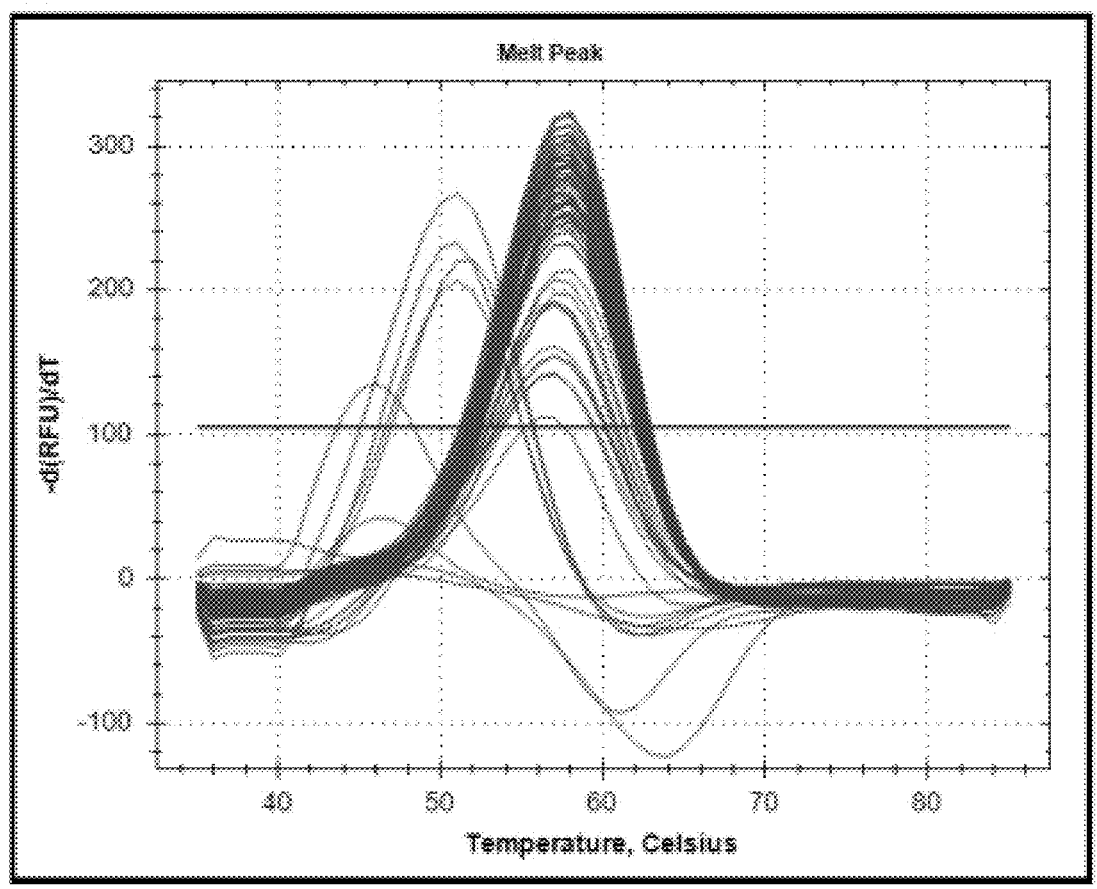
Figure 3:
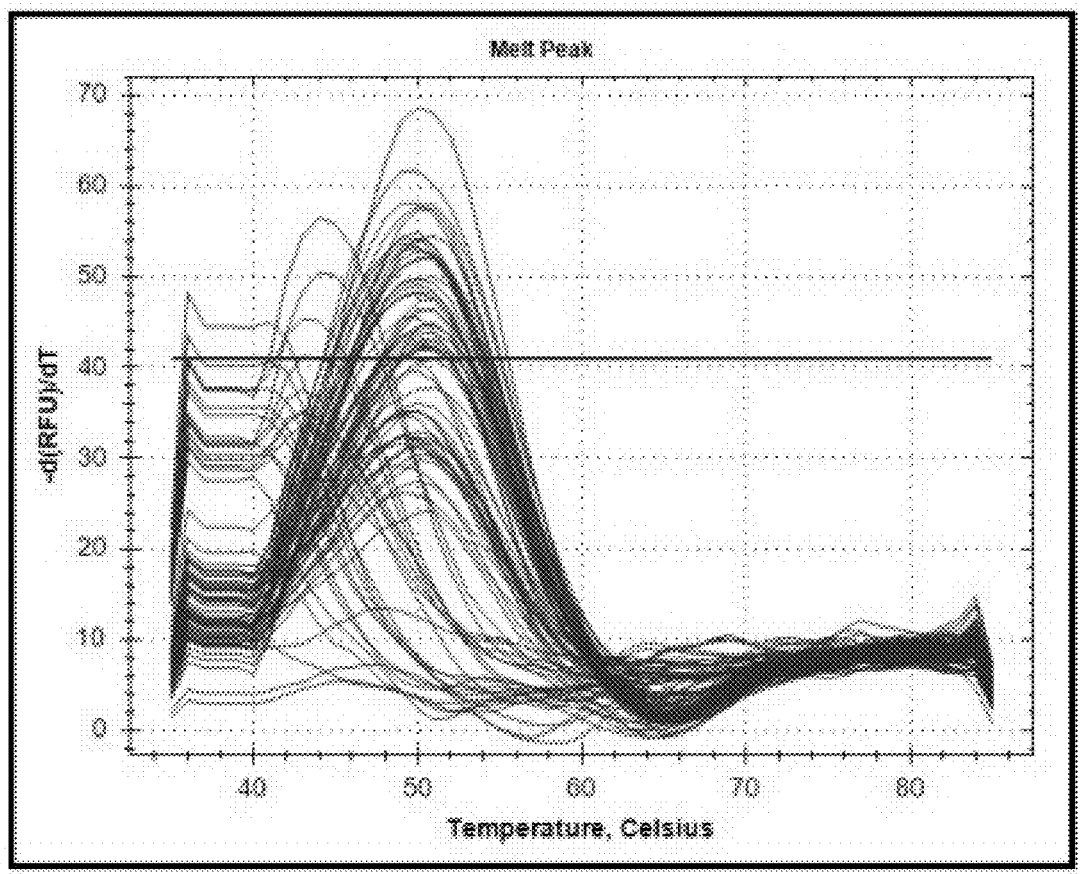
Figure 3:
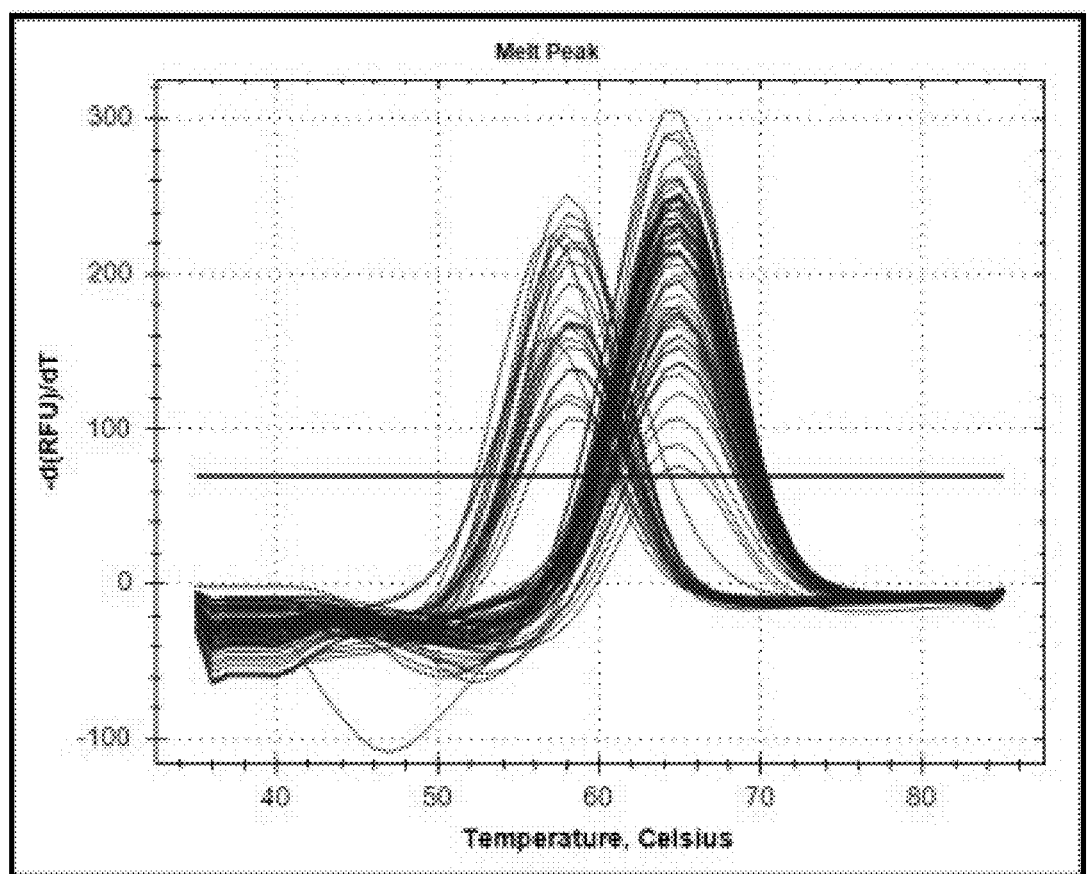
Figure 3:
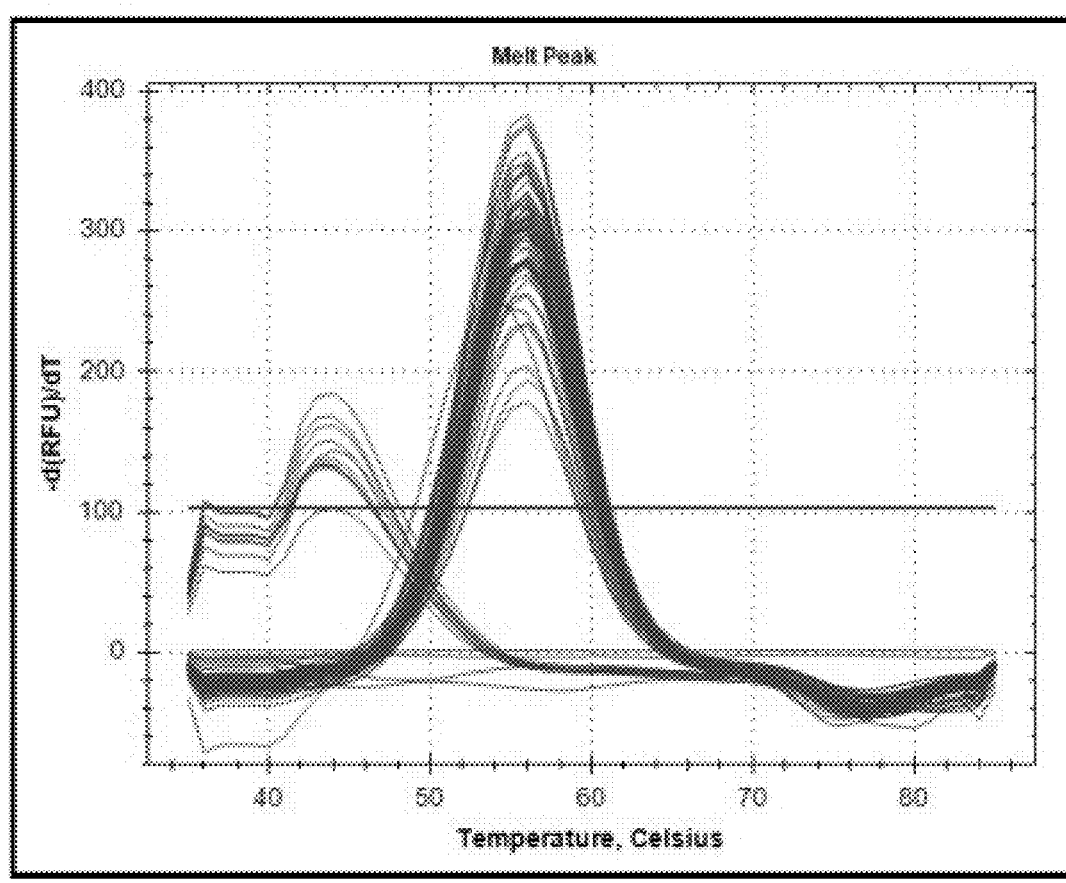
Figure 3:
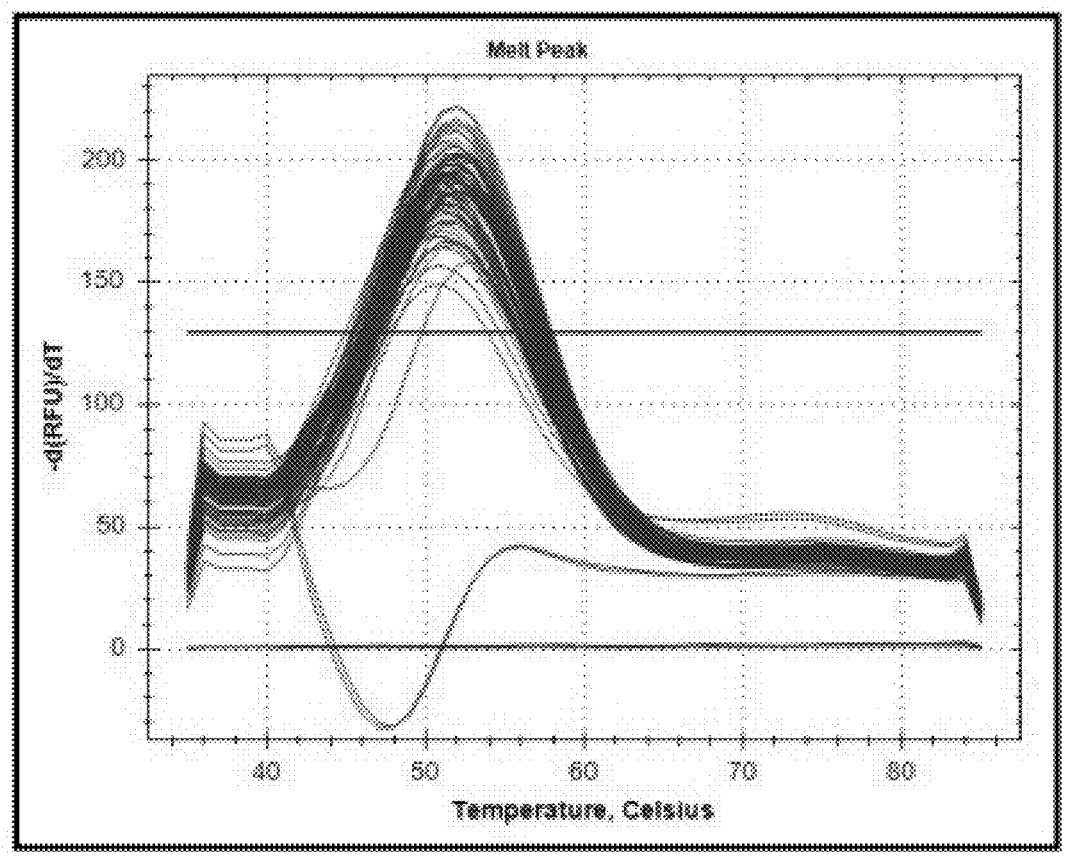

According to an exemplary embodiment of the present invention, in order to perform the SNP analysis using mtDNA as a template, the 16 PNA probes and the samples (used samples) synthesized in Example 1 were amplified, and the melting curve analysis was performed on the resultant mtDNA amplification products and the PNA probes. As a result, it was confirmed that melting temperature (Tm) difference was caused by the incomplete hybridization with the PNA probes due to base mutation or base deletion of the mtDNA base sequence (FIG. 2b and FIG. 3).

Another aspect of the present invention relates to a kit for analyzing SNP of mtDNA, comprising the PNA probes labeling the reporter and the quencher labeled thereto and hybridizing to a base sequence of mtDNA.

The PNA probes comprises PNA probes of SEQ ID NOs 1 to 9, which hybridize to the HV 1 region or of SEQ ID NOs 10 to 16, which hybridize to the HV 2 region.

The present invention may comprise optionally a primer set, a buffer, and a DNA polymerase cofactor for amplification of mtDNA, and a reagent necessary to perform a target amplification PCR reaction (e.g., PCR reaction) such as deoxyribonucleotide-5-triphosphate. Alternatively, the kit of the present invention may also include various polynucleotide molecules, reverse transcriptase, various buffers and reagents, and antibodies inhibiting DNA polymerase activity.

Further, the optimal amount of reagent used in a particular reaction for the kit can be readily determined by those skilled in the art having the teachings herein. Typically, the kit of the present invention is prepared as a separate package or compartment containing the aforementioned components.

Another aspect of the present invention relates to a method for providing information for human identification, comprises: (a) hybridizing mtDNA of an subject's sample with a plurality of PNA probes to which a reporter and a quencher are labeled and to be hybridized with a base sequence of mtDNA; (b) obtaining melting temperature (Tm) of the mtDNA and the PNA probes for each of the PNA probes by melting the hybridized product while changing the temperature; and (c) grouping the Tm obtained for each of the PNA probes to give codes to the probes.

In order to analyze a base sequence of mtDNA, the present invention may provide information on coding of the Tm of the mtDNA and the PNA probe.

According to an exemplary embodiment of the present invention, the Tm of the mtDNA and the PNA probe may be grouped so that the Tm groups are different from each other and receive separate codes.

As a result of analyzing the melting curve of mtDNA of the test sample using a base sequence coding method of mtDNA according to the present invention, it was confirmed that the Tm are the same or different from each other depending on whether the base sequence of the sample hybridized with one PNA probe is mutated and that combinations of Tm were different from each other depending on the test sample when the analysis is simultaneously performed using two or more PNA probes. When such features are used, a reference code can be prepared using a probe. As a result, the code can be given as shown in FIG. 5.

As the PNA probe is not completely hybridized with the base sequence of the sample, the base sequence change can be confirmed by the Tm shifts. When a series of codes are given to a plurality of Tm according to the respective base sequence changes, it is possible to analyze a large amount of samples and to keep track of the samples. Further, classification of Tm of a new sample based on the coding method of the samples to which codes have been preliminarily given can facilitate identification by mtDNA code information such as paternity identification, suspect DNA comparison, and casualty identification.

Figure 5:
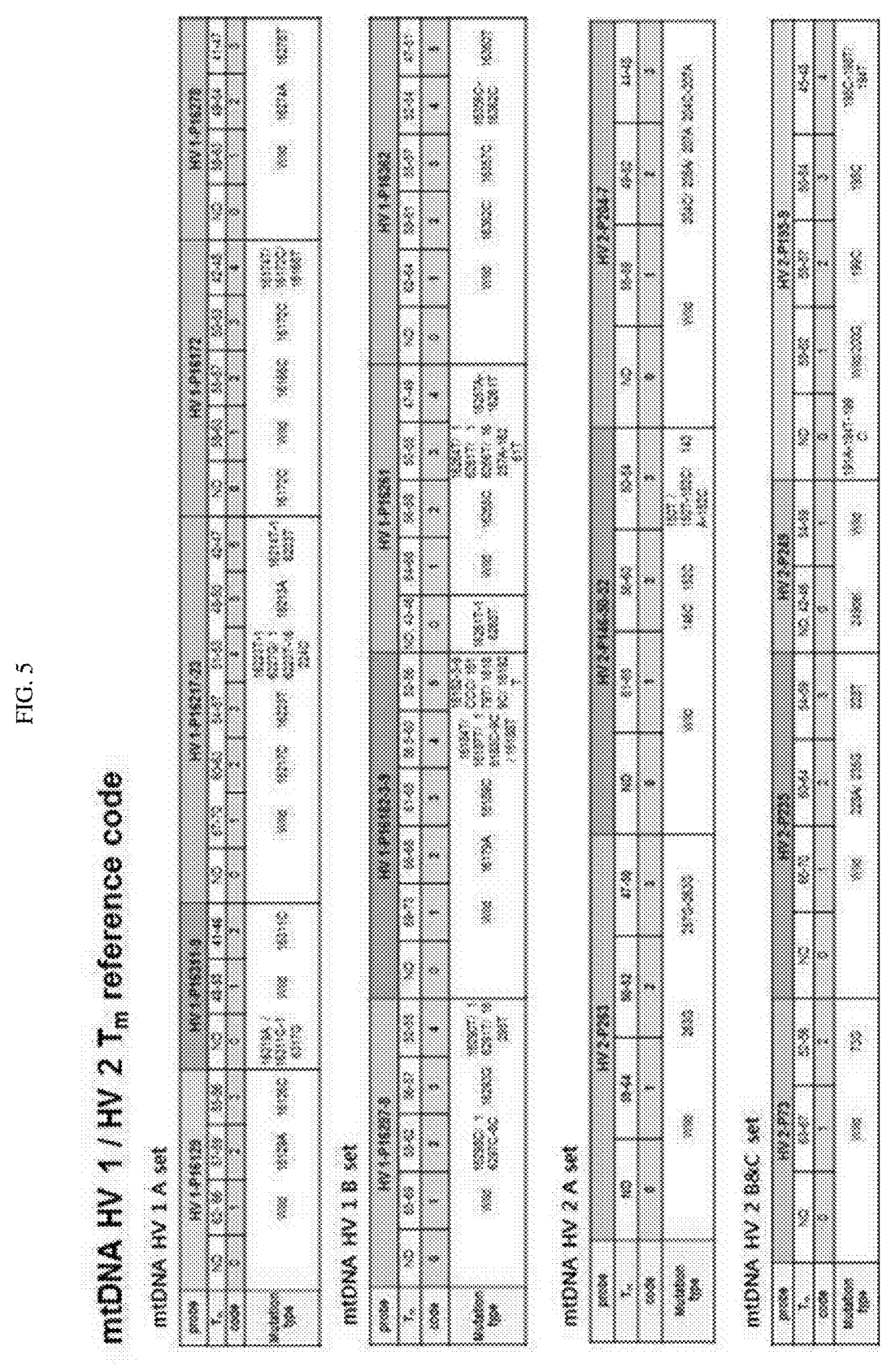

As illustrated in FIG. 5, when the coding method of the present invention is used, it is possible to prepare a minimal PNA probe complementarily binding to a base sequence in which base sequence variation of mtDNA frequently occurs, for example, a hypervariable (HV) 1 or 2 region, and to encode the melting curves, and thereby there is no need for a separate analysis program for identification. According to an exemplary embodiment of the present invention, it is confirmed that 73 samples can be identified by 16 probes.

According to coding for the individual identification of the present invention, one PNA probe exhibits various Tm depending on whether the base sequence is changed and thus these are appropriately combined to be represented by numerals, so that the information on each sample can be confirmed, and as the range of Tm is grouped, the smaller the number of PNA probes, the more information can be coded. The Tm can be grouped into the temperature range of 40° C. to 95° C., which enables the measurement of the melting curve and the range of 5° C. to 95° C. depending on the equipment. However, although the positions of base sequences are different from each other, the Tm thereof may be the same. In this case, additional PNA probes can be designed to identify them.

Figure 4:
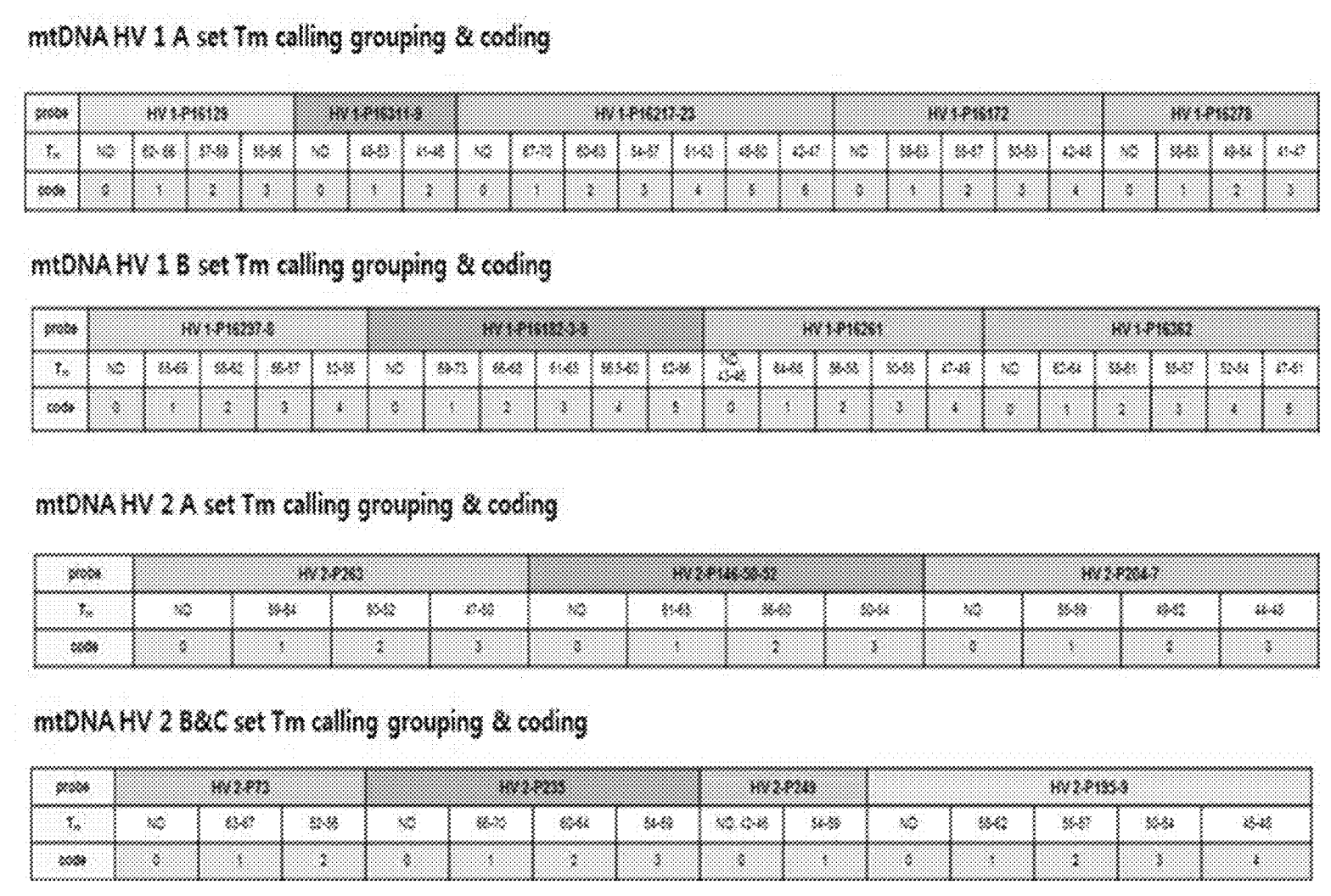

As a result of analyzing the melting curve of mtDNA using the human identification code method of the present invention, it is possible to group the Tm and assign a code to each probe as shown in FIG. 4. When a series of codes are assigned to the Tm based on each base sequence change, the code itself may be used for identification including base sequence information. Further, the simplicity of information through code has the advantage of being very easy to manage and track.

According to an exemplary embodiment of the present invention, the melting curve temperature was classified according to each of the probes, then each number was assigned, and then the coding was performed for each sample (FIG. 4). The result was compared with the result of Sanger sequencing, and the reference sequence was prepared according to the mtDNA base sequence (FIG. 5).

As a result of the comparison of the coding information for each of the above samples and the reference sequence, it was possible to confirm unique mtDNA base sequence information that matches Sanger sequencing result at a specific temperature of the probe (Example 3).

In other words, it was confirmed that the identification can be quickly and effectively performed when the melting curves of the sample containing the mtDNA and the PNA probe is analyzed by comparing coding of samples with the reference code.

Hereinafter, the present invention will be described in more detail with reference to examples. These embodiments are only for illustrative purposes, and it will be apparently understood by those skilled in the art that the scope of the present invention is not construed as being limited by these Examples.

EXAMPLE

Hereinafter, the present invention will be described in more detail with reference to Examples. These Examples are only for illustrative purposes, and it will be apparently understood by those skilled in the art that the scope of the present invention is not construed as being limited by these Examples.

Example 1

PNA Probe Design of Mitochondrial DNA (mtDNA) for Identification

PNA probes were directly designed for analyzing base sequences. All PNA probes (FAM-labeled, Dabcyl) used in the present invention were synthesized by HPLC purification method from Panagene (Korea). The purity of all synthesized probes was confirmed by mass spectrometry. The unnecessary secondary structures of the probes were excluded for more effective coupling with the target SNP. Further, the structural characteristics of artificial synthetic oligo with fluorescent labeling were made by crossing the positions of the fluorescent reporter and the quencher on the production of the PNA probes.

Further, melting temperature (Tm) of a mutated portion of a base was designed to be differentiated based on the designed PNA probe by complementary binding of artificial synthetic oligos (Table 1).

TABLE 1

| Name | Sequence (5'→3') | Remark | SEQ ID NO. |
| --- | --- | --- | --- |
| HV 1-P16129 | Dabcyl-ATA TTG TAC GGT ACC ATA-O-K (HEX) | HV 1 A SET | 1 |
| HV 1-P16311-9 | FAM-GTA CAT AAA GC-O-K (Dabcyl) | PNA probe | 2 |
| HV 1-P16172 | Dabcyl-Lys(Dabcyl)-AAC CCA ATC CAC A-O-K (TxR) | | 3 |
| HV 1-P16278 | Dabcyl-Lys(Dabcyl)-AGG ATA CCA ACA A-O-K (Alexa 680) | | 4 |
| HV 1-P16217-23 | Dabcyl-AGT AAT CAA CCC TCA AC-O-K (Cy5) | | 5 |
| HV 1-P16261 | Dabcyl-CAC CCC TCA CCC AC-O-K (Cy5) | HV 1 B SET | 6 |
| HV 1-P16297-8 | Dabcyl-ACC TAC CCA CCC TTA ACA-O-K (HEX) | PNA probe | 7 |
| HV 1-P16182-3-9 | Dabcyl-ATC AAA ACC CCC TCC CCA T-O-K (FAM) | | 8 |
| HV 1-P16362 | Dabcyl-ATC CCT TCT CGT CCC AAT G-O-K(TxR) | | 9 |
| HV 2-P146-50-52 | Dabcyl-TTC CTG CCT CAT CCT ATT ATT TA-O-K (FAM) | HV 2 A SET PNA probe | 10 |
| HV 2-P263 | Dabcyl-ACA GCC ACT TTC CAC A-O-K (HEX) | | 11 |
| HV 2-P204-7 | TxR-AGT GTG TTA ATT AAT TAA T-O-K (Dabcyl) | | 12 |
| HV 2-P235 | Dabcyl-GTA GGA CAT AAT AAT AAC A-O-K (FAM) | HV 2 B SET PNA probe | 13 |
| HV 2-P249 | TxR-ATT GAA TGT CTG C-O-K(Dabcyl) | | 14 |
| HV 2-P195-9 | Dabcyl-GCG AAC ATA CTT ACT AA-O-K(HEX) | | 15 |
| HV 2-P73 | Dabcyl-GGG TAT GCA CGC-O-K (Cy5) | HV 2 C SET PNA probe | 16 |

(In Table 1 as describe above, TxR represents Texas red. Further, Dabcyl refers to a quencher, and FAM, Texas red, HEX, Alexa 680, and Cy5 refer to reporters.)

As shown in Table 1, 9 HV 1 regions and 7 HV 2 regions were designed in case of the PNA probes designed for analyzing mtDNA SNP. A total of 16 probes were used to identify 62 mtDNA SNPs (HV 1:42, HV 2:20) so that identification can be confirmed (FIG. 1).

Example 2

Melting Curve Analysis of mtDNA SNP 73 samples stored Korean National Forensic Service (NFS) were used in the experiments as samples for mtDNA base sequence analysis. For positive controls, reference sequences of HV 1 and HV 2 regions were constructed using NCBI DB. The 73 samples were samples that had been subjected to genetic analysis of mtDNA by Sanger sequencing.

The mtDNA amplification product obtained by performing PCR using the sample as a template was mixed with the probe set synthesized in Example 1. Then the melting curve analysis was performed using a CFX96™ Real-Time system (BIO-RAD Corporation, USA). The experimental conditions are followings for the mtDNA base sequence analysis using the PNA probe.

First, for HV 1 mtDNA genotype analysis, 3 μl of the HV 1 gene product obtained after the gene amplification, 1 μl/50 pmol of the primer HV 1-R, 0.5 μl/10 pmol of the PNA probe A set (HV 1-P16129, HV 1-P16311-9, HV 1-P16172, HV 1-P16278, and HV 1-P16217-23), and 5.5 μl of distilled water were added to prepare mtDNA HV 1 A set. For HV 1 B set, the gene product and primer used in the preparation of the A set were added in the same manner, and 0.5 μl/10 pmol of the PNA probe B set (HV 1-P16261, HV 1-P16297-8, HV 1-P16182-3-9, and HV 1-P16362) was added to prepare HV 1 B set.

On the other hand, for HV 2, 3 μl of the gene amplification product for HV 2 mtDNA genotype analysis, 1 μl/50 pmol of the primer HV 2-R, 0.5 μl/10 pmol of the PNA probe A set (HV 2-P146-50-52, HV 2-P263, and HV 2-P204-7), and 5.5 μl of distilled water were added to prepare a set of mtDNA HV 2 A. For HV 2 B set, the gene product and primer used in the preparation of HV 2 A set were added in the same manner, and 0.5 μl/10 pmol of the set B (HV 2-P235, HV 2-P249 and HV 2-P195-9) was added to prepare mtDNA HV 2 B set. For the HV 2 C set, the gene product and primer used in the preparation of the HV 2 A set were added in the same manner, and 0.5 μl/10 pmol of HV 2 C set (HV 2-P73) was added to prepare mtDNA HV 2 C set.

Analysis of mtDNA base sequence was performed on HV 1 and HV 2 positive control samples and 73 human samples. Melting curve analysis was carried out by denaturing at 95° C. for 5 minutes, followed by hybridization at 75° C., 55° C. and 45° C. for 1 minute each, and followed by increasing the temperature from 30° C. to 85° C. by 1.0° C./5 seconds with measurement of fluorescence thereof (FIGS. 2a and 2b).

Figure 2A:
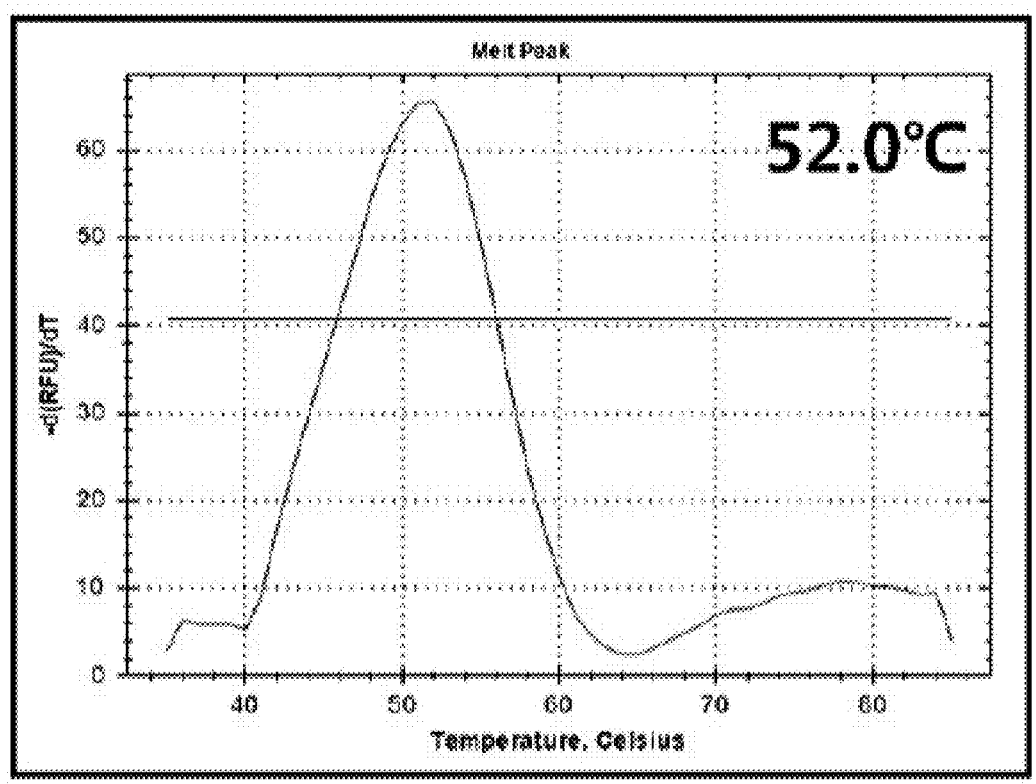
FIGS. 2a and 2b show the melting curve analysis of the positive control group (FIG. 2a) and the melting curve analysis of the 73 human samples (FIG. 2b).
Figure 2A:
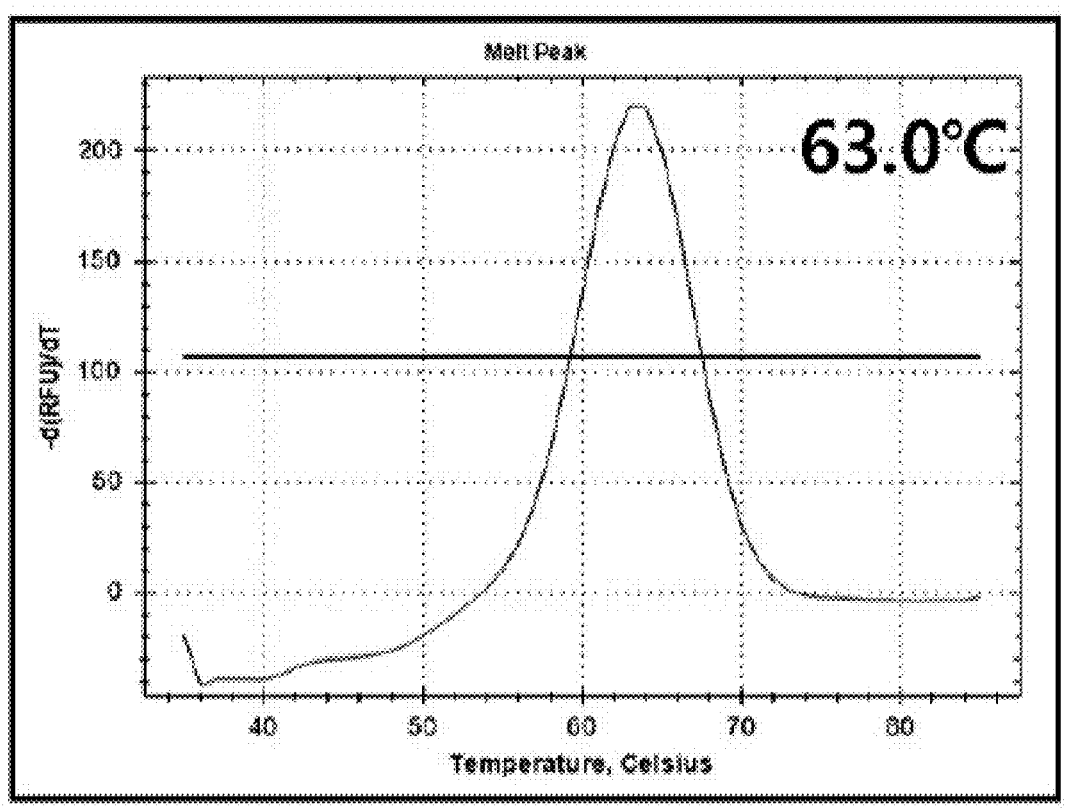
Figure 2A:
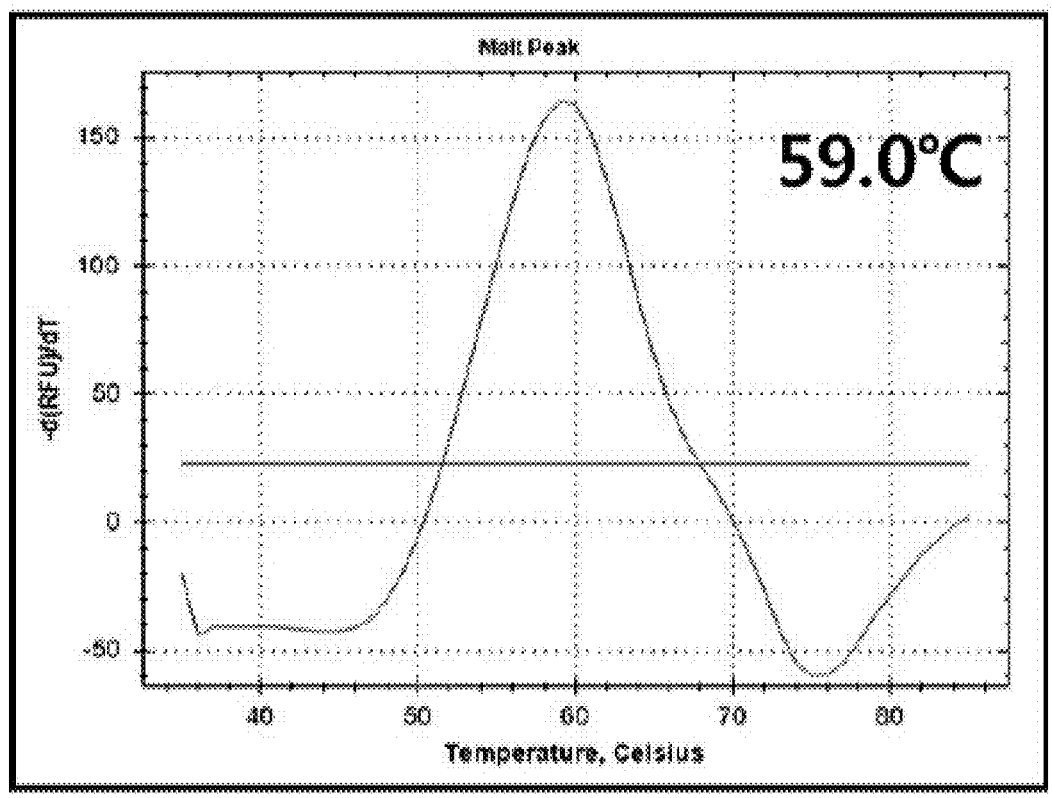
Figure 2A:
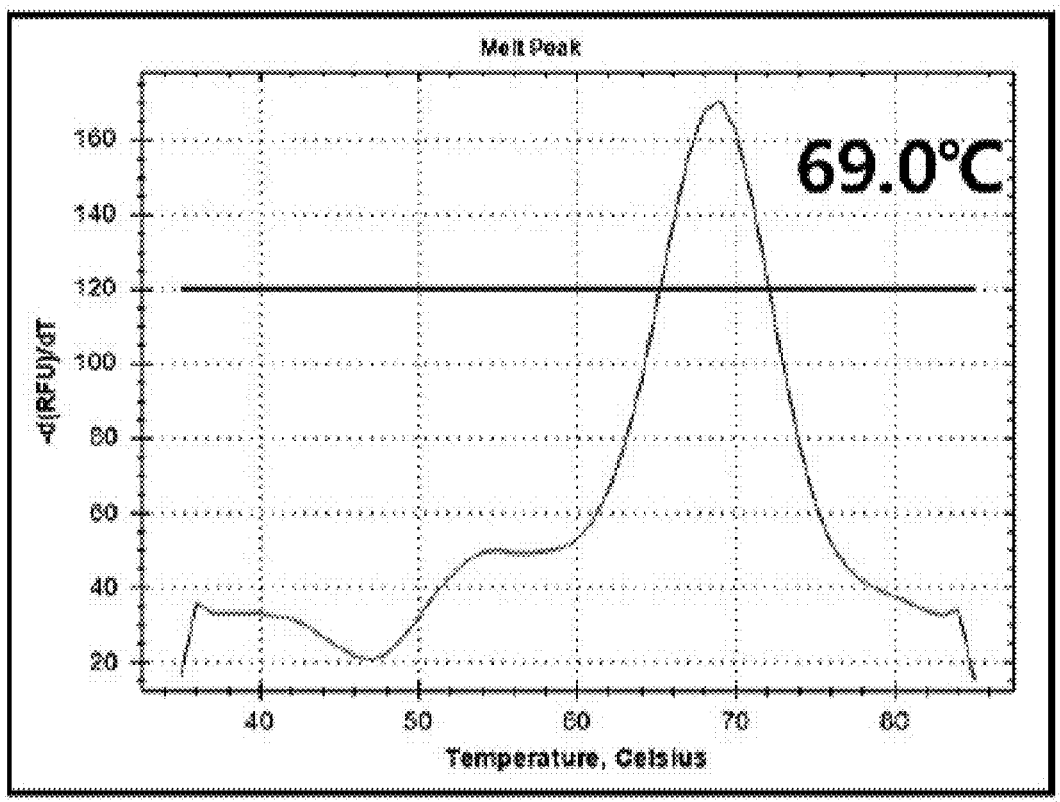
Figure 2A:
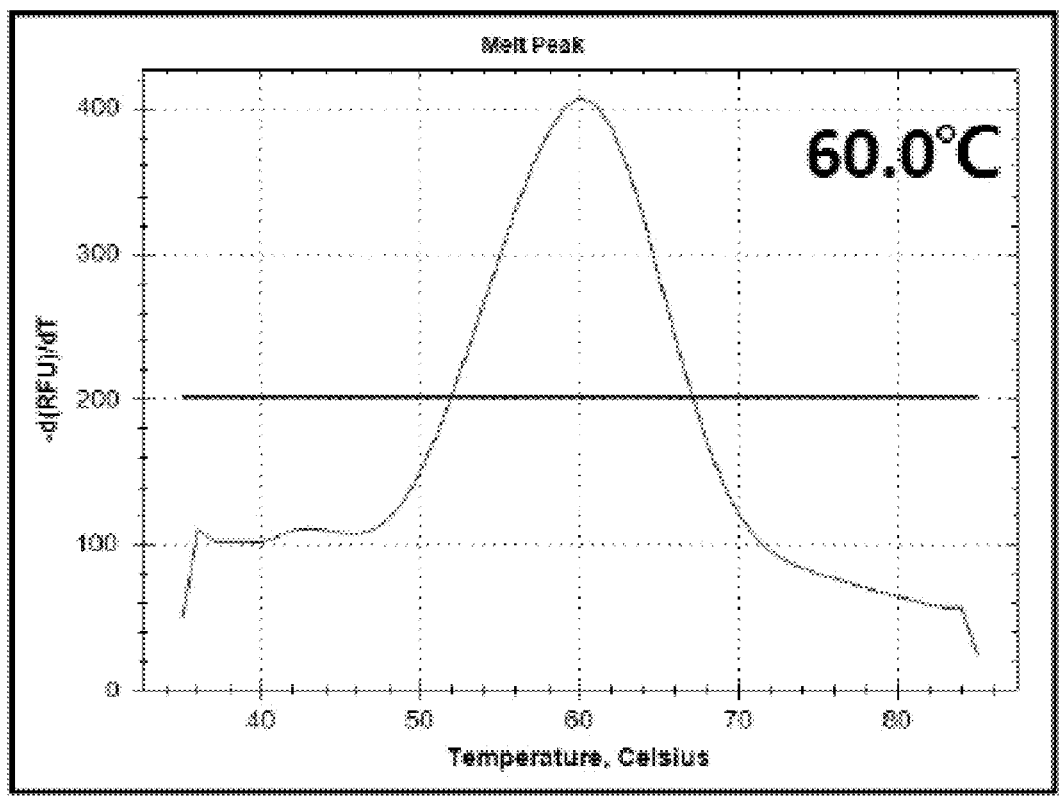
Figure 2A:
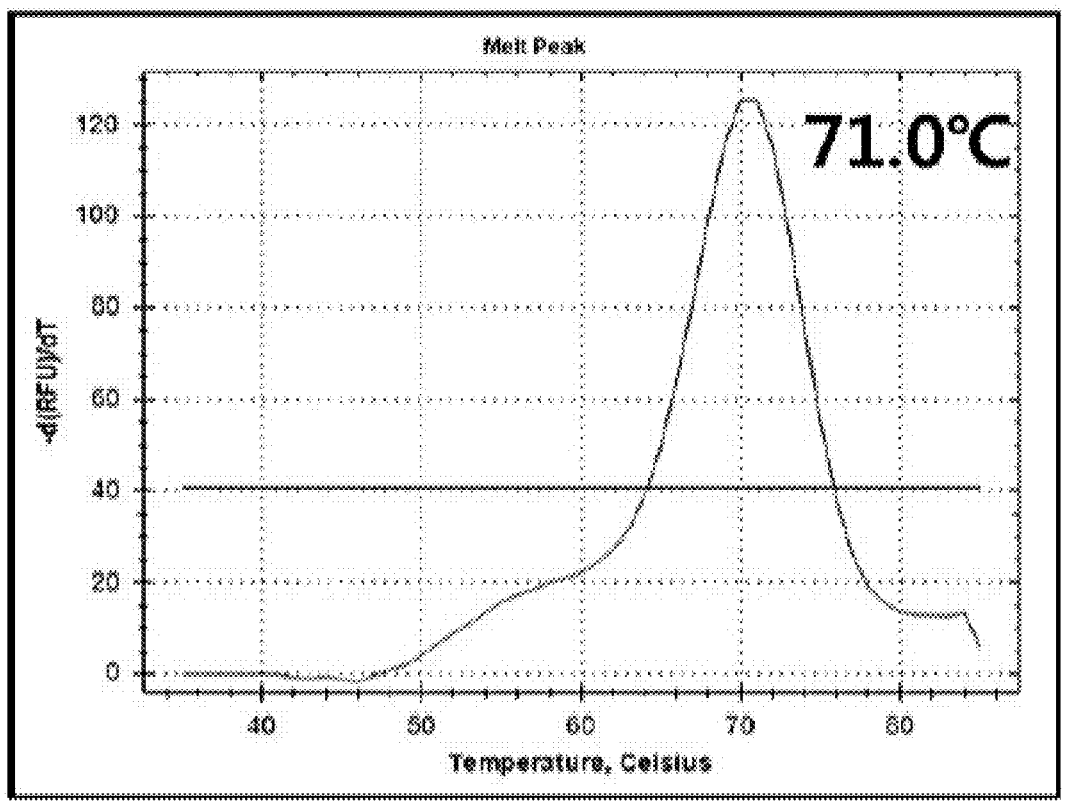
Figure 2A:
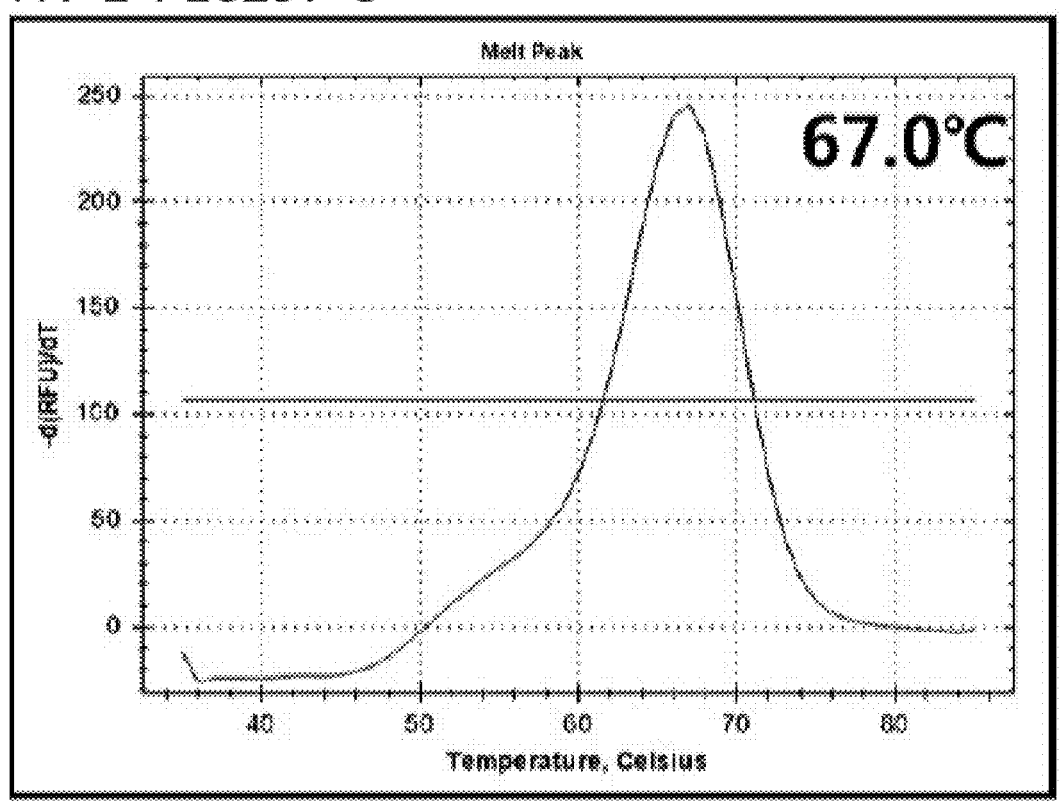
Figure 2A:
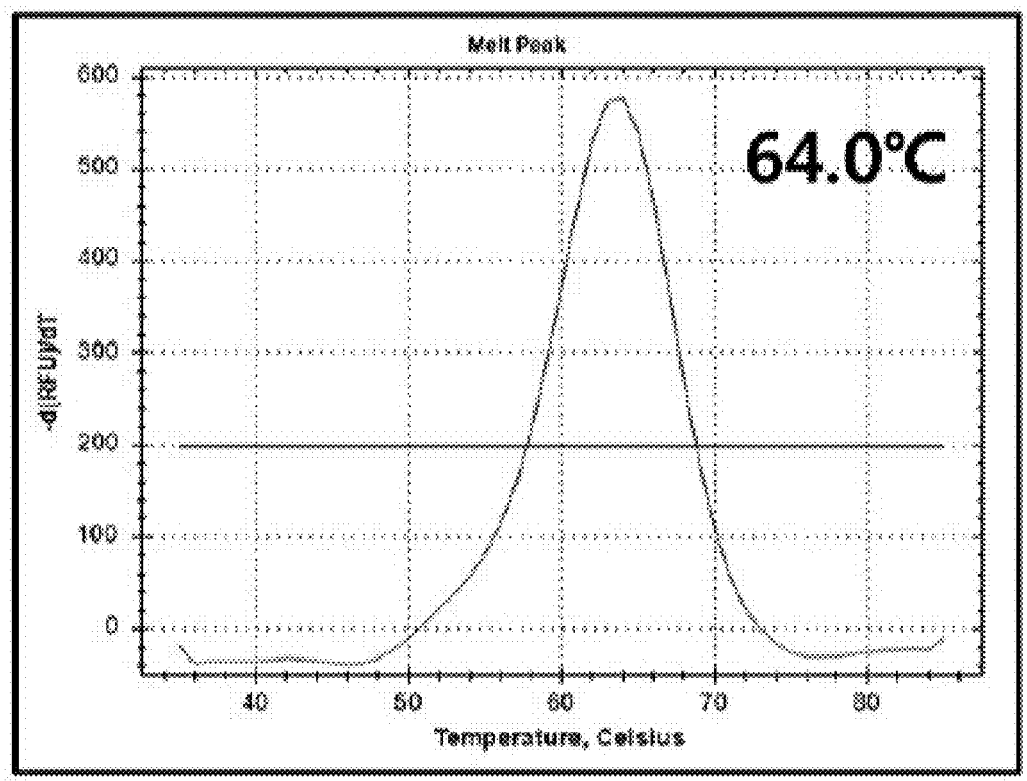
Figure 2A:
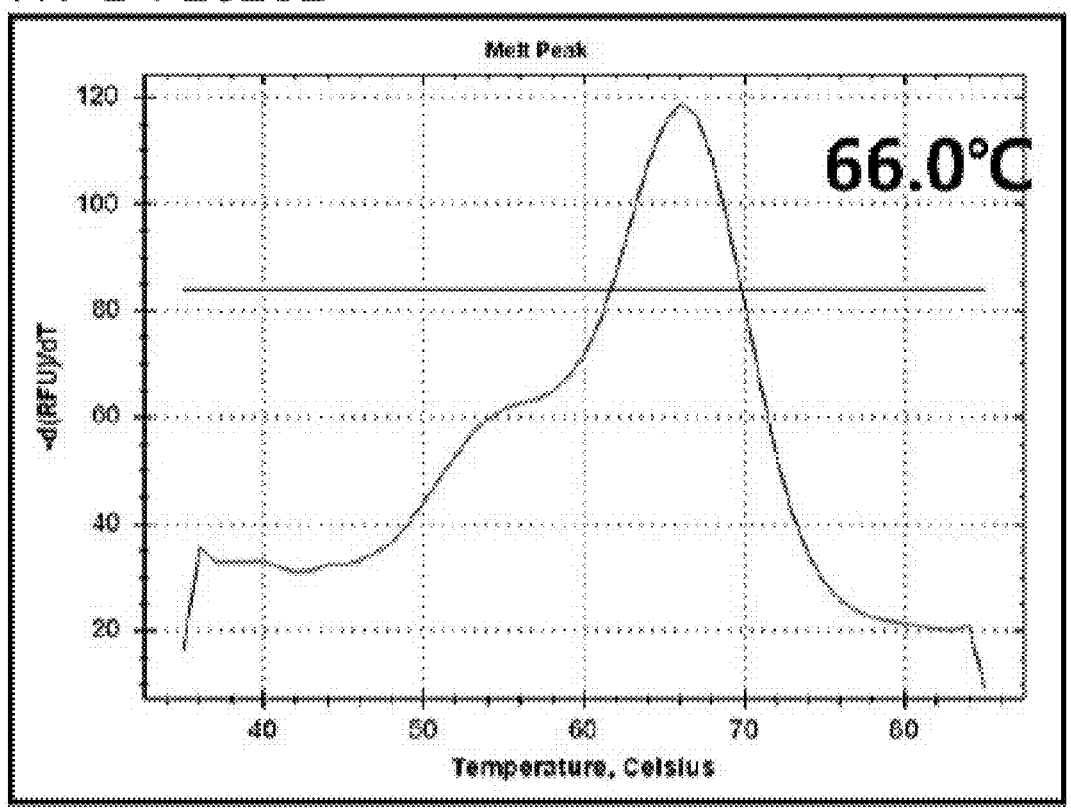
Figure 2A:
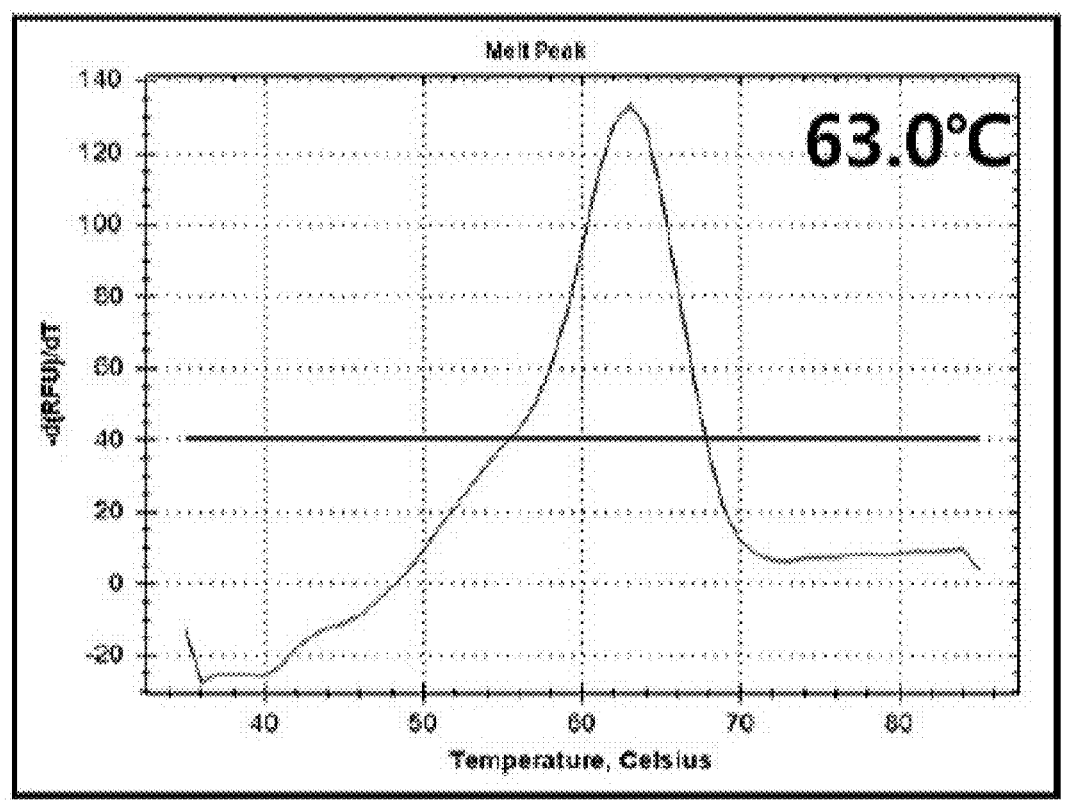
Figure 2A:
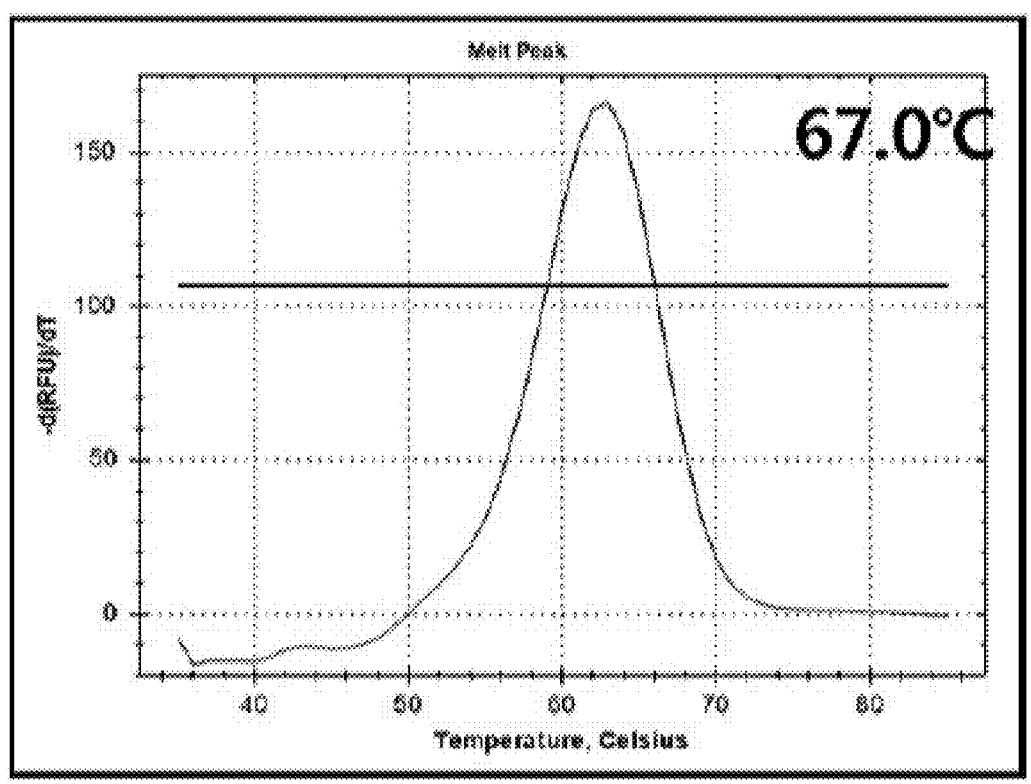
Figure 2A:
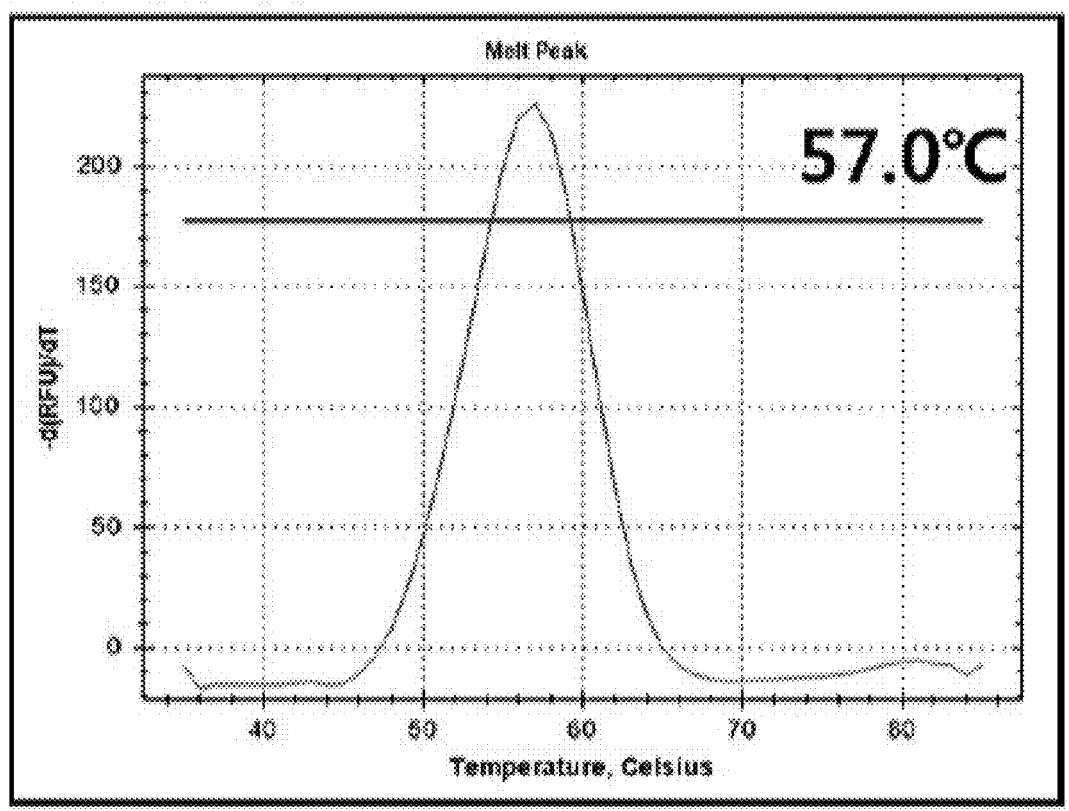
Figure 2A:
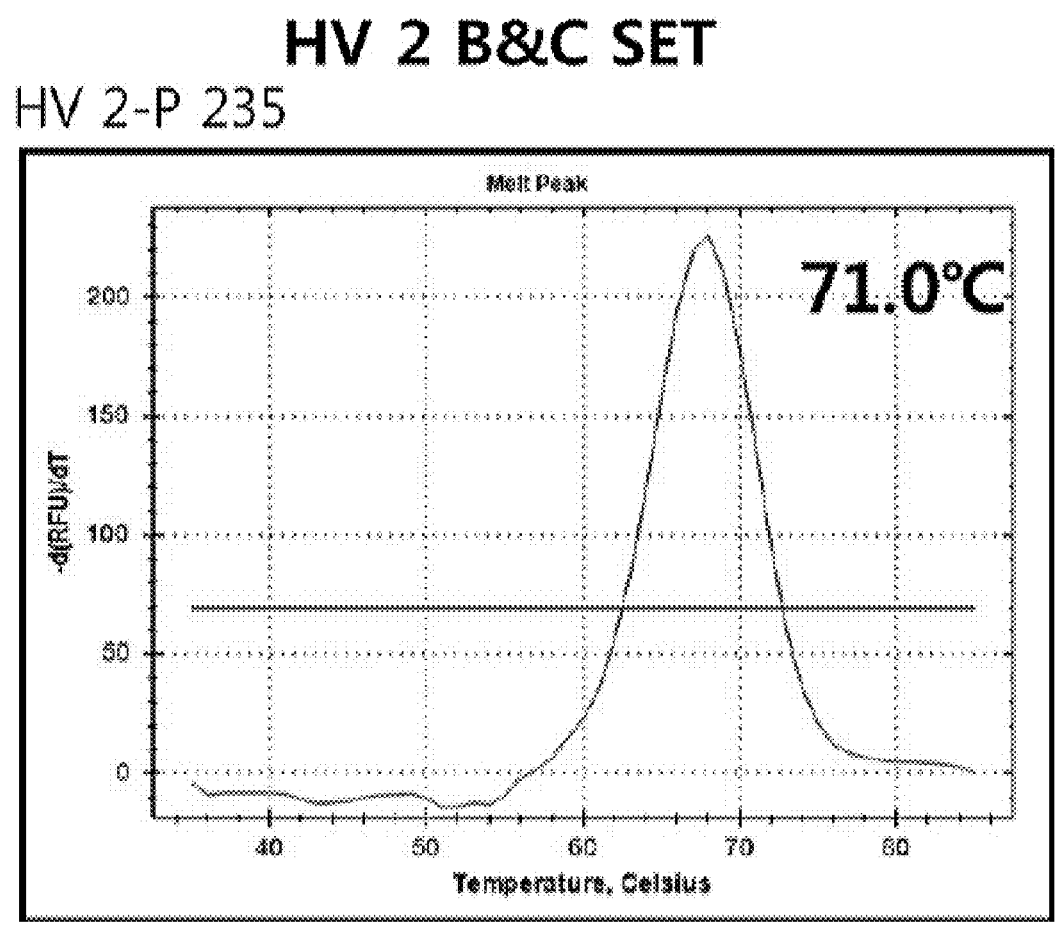
Figure 2A:
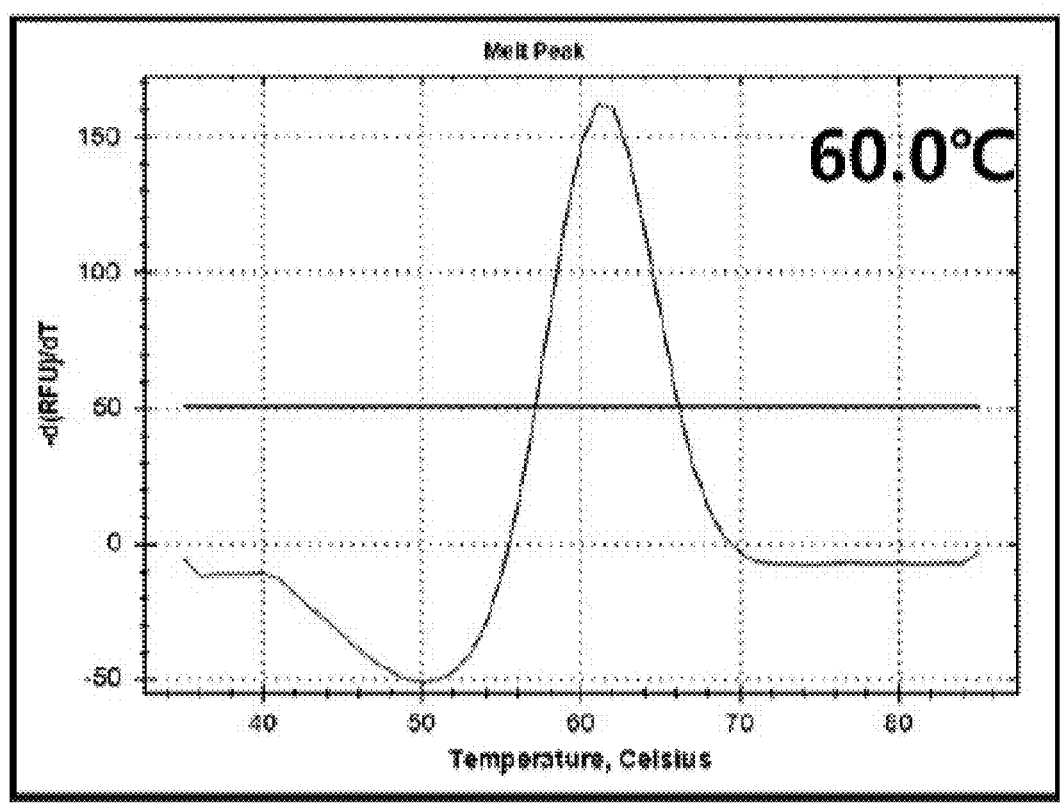
Figure 2A:
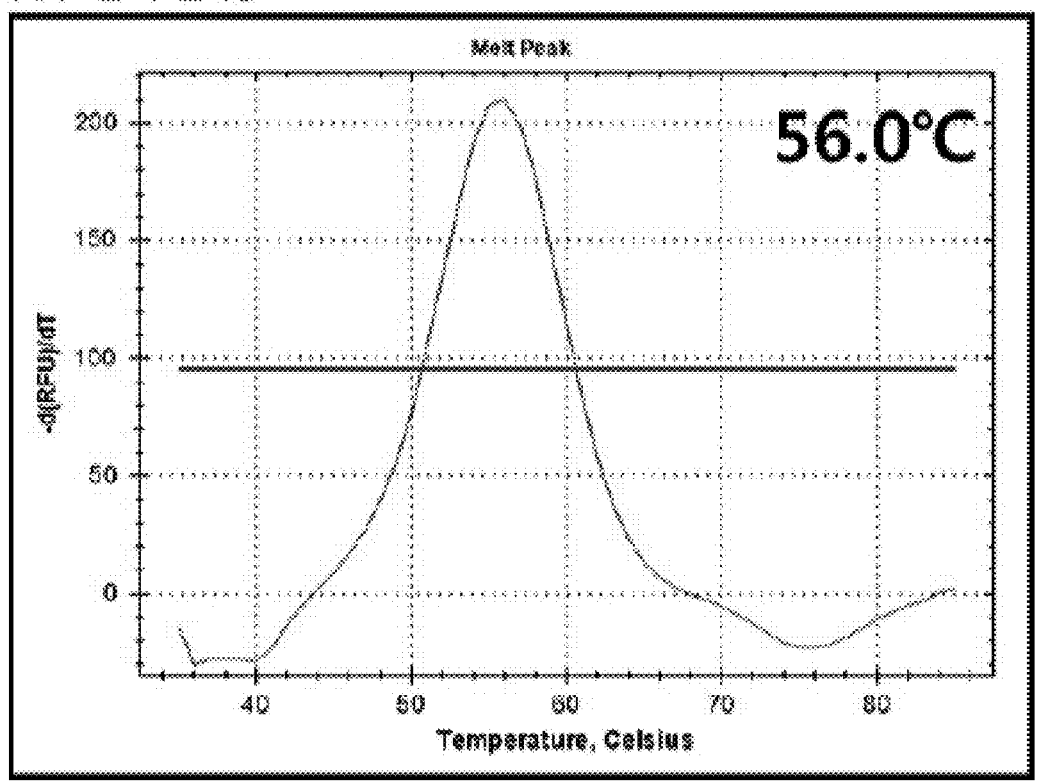
Figure 2A:
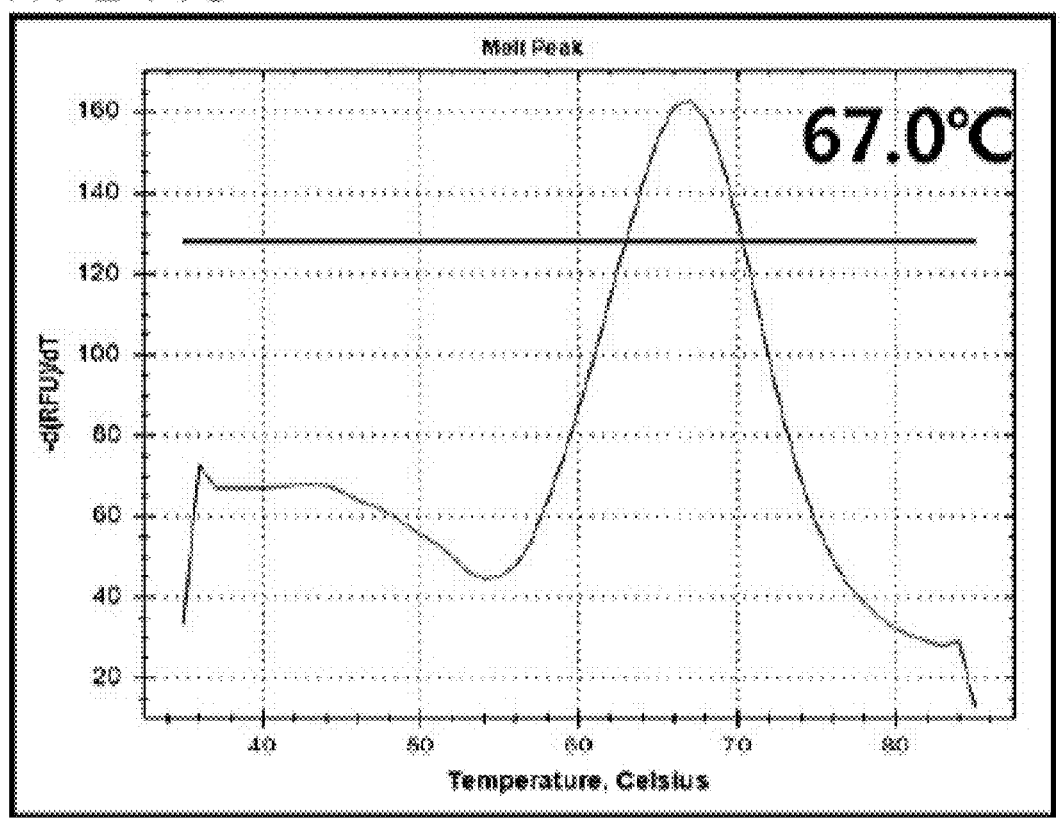

As a result of the melting curve analysis using the positive control group, it was confirmed that the PNA probe designed for the analysis of the synthesized base sequence exhibited the inherent melting curve temperature to be correctly grouped (FIG. 2a). Further, the melting curve analysis were summarized by sets and probes for mtDNA base sequence analysis of 73 samples on the basis of the positive control group (FIG. 4).

Example 3

Coding of mtDNA Base Sequence Information Using PNA Probes (N-Code)

Based on the melting curve analysis of Example 2, the melting curve temperatures were grouped by probe and numbered, and 73 samples were number-coded (Table 4). Further, reference codes according to mtDNA base sequence were prepared by comparing with the result of Sanger sequencing (FIG. 5).

As shown in FIG. 5, such results were sorted by the results of Sanger sequencing of 73 samples through the grouping of the melting temperature of the probes in FIG. 4 to confirm inherent mtDNA base sequence information consistent with the result of Sanger sequencing at the specific temperature of the probe. The positions of mtDNA base sequence information on 73 samples were arranged in order based on the reference codes of FIG. 5, and then the mtDNA base sequence information on the entire HV 1 and HV 2 regions was coded.

As a result of the melting curve analysis using the PNA probes, it was confirmed that the mtDNA base sequence information that can be used for identity confirmation was 100% consistent with the result of Sanger sequencing.

According to the present invention, the method for analyzing SNP of mtDNA uses PNA probes labeled with the reporter and the quencher so that time and cost required for individual identification can be drastically decreased, initial analysis can be carried out in the event of a large number of inspections or mass casualties, and human identification information can be coded, and thus it is very easy to manage and supervise the same.

The specific portion of the present invention is described in detail as described above. It will be apparent to those skilled in the art that such specific descriptions are only preferred embodiments and that the scope of the present invention is not limited thereby. Accordingly, the actual scope of the present invention will be defined by the appended claims and their equivalents.

What is claimed is:

1. A method for analyzing SNPs of mitochondrial DNA (mtDNA), comprising:
   (a) hybridizing mtDNA of a subject's sample with PNA probes of SEQ ID NOs: 1 to 9 that hybridize to the HV 1 region of the mtDNA or PNA probes of SEQ ID NOs: 10 to 16 that hybridize to the HV 2 region of the mitochondrial DNA (mtDNA), wherein each of said PNA probes is labeled with a reporter and a quencher;
   (b) obtaining a melting curve by melting the hybridized products while changing the temperature; and
   (c) determining SNPs in the mtDNA by a melting curve analysis of said melting curve.

2. The method of claim 1, wherein the reporter is one or more selected from the group consisting of FAM (6-carboxyfluorescein), Texas red, HEX (2',4',5',7'-tetrachloro-6-carboxy-4,7-dichlorofluorescein), Alexa 680 and Cy5.

3. The method of claim 1, wherein the quencher is one or more selected from the group consisting of TAMRA (6-carboxytetramethyl-rhodamine), BHQ1, BHQ2 and Dabcyl.

4. A kit for analyzing SNPs of mitochondrial DNA (mtDNA), comprising PNA probes of SEQ ID NOs 1 to 9 that hybridize to the HV 1 region of the mtDNA or PNA probes of SEQ ID NOs 10 to 16 that hybridize to the HV 2 region of the mtDNA, wherein each of said PNA probes is labeled with a reporter and a quencher.

5. The kit of claim 4, wherein the reporter is one or more selected from the group consisting of FAM (6-carboxyfluorescein), Texas red, HEX (2',4',5',7'-tetrachloro-6-carboxy-4,7-dichlorofluorescein), Alexa 680 and Cy5.

6. The kit of claim 4, wherein the quencher is one or more selected from the group consisting of TAMRA (6-carboxytetramethyl-rhodamine), BHQ1, BHQ2 and Dabcyl.

7. A method for providing information for personal identification, comprising:
   (a) hybridizing mitochondrial DNA (mtDNA) of a subject's sample with PNA probes of SEQ ID NOs 1 to 9 that hybridize to the HV 1 region of the mtDNA or PNA probes of SEQ ID NOs 10 to 16 that hybridize to the HV 2 region of the mtDNA, to yield hybridized product, wherein each of said PNA probes is labeled with a reporter and a quencher;
   (b) obtaining melting temperature (Tm) of the mtDNA and the PNA probes, for each of the PNA probes, by melting the hybridized product while changing the temperature; and
   (c) grouping the melting temperatures obtained for each of the PNA probes to give codes to the probes according to the melting temperature of each probe, for said personal identification.

8. The method of claim 7, wherein the reporter is one or more selected from the group consisting of FAM (6-carboxyfluorescein), Texas red, HEX (2',4',5',7'-tetrachloro-6-carboxy-4,7-dichlorofluorescein), Alexa 680 and Cy5.

9. The method of claim 7, wherein the quencher is one or more selected from the group consisting of TAMRA (6-carboxytetramethyl-rhodamine), BHQ1, BHQ2 and Dabcyl.

* * * * *

SEQUENCE LISTING

<160> NUMBER OF SEQ ID NOS: 16

<210> SEQ ID NO 1
<211> LENGTH: 18
<212> TYPE: DNA
<213> ORGANISM: Artificial Sequence
<220> FEATURE:
<223> OTHER INFORMATION: HV 1 -P16129

<400> SEQUENCE: 1
atattgtacg gtaccata                                                18

```
<210> SEQ ID NO 2
<211> LENGTH: 11
<212> TYPE: DNA
<213> ORGANISM: Artificial Sequence
<220> FEATURE:
<223> OTHER INFORMATION: HV 1 -P16311-9

<400> SEQUENCE: 2
gtacataaag c                                                          11

<210> SEQ ID NO 3
<211> LENGTH: 13
<212> TYPE: DNA
<213> ORGANISM: Artificial Sequence
<220> FEATURE:
<223> OTHER INFORMATION: HV 1 -P16172

<400> SEQUENCE: 3
aacccaatcc aca                                                        13

<210> SEQ ID NO 4
<211> LENGTH: 13
<212> TYPE: DNA
<213> ORGANISM: Artificial Sequence
<220> FEATURE:
<223> OTHER INFORMATION: HV 1 -P16278

<400> SEQUENCE: 4
aggataccaa caa                                                        13

<210> SEQ ID NO 5
<211> LENGTH: 17
<212> TYPE: DNA
<213> ORGANISM: Artificial Sequence
<220> FEATURE:
<223> OTHER INFORMATION: HV 1 -P16217-23

<400> SEQUENCE: 5
agtaatcaac cctcaac                                                    17

<210> SEQ ID NO 6
<211> LENGTH: 14
<212> TYPE: DNA
<213> ORGANISM: Artificial Sequence
<220> FEATURE:
<223> OTHER INFORMATION: HV 1 -P16261

<400> SEQUENCE: 6
cacccctcac ccac                                                       14

<210> SEQ ID NO 7
<211> LENGTH: 18
<212> TYPE: DNA
<213> ORGANISM: Artificial Sequence
<220> FEATURE:
<223> OTHER INFORMATION: HV 1 -P16297-8

<400> SEQUENCE: 7
acctacccac ccttaaca                                                   18

<210> SEQ ID NO 8
<211> LENGTH: 19
<212> TYPE: DNA
<213> ORGANISM: Artificial Sequence
<220> FEATURE:
```

<223> OTHER INFORMATION: HV 1 -P16182-3-9

<400> SEQUENCE: 8
atcaaaaccc cctccccat                                                19

<210> SEQ ID NO 9
<211> LENGTH: 19
<212> TYPE: DNA
<213> ORGANISM: Artificial Sequence
<220> FEATURE:
<223> OTHER INFORMATION: HV 1 -P16362

<400> SEQUENCE: 9
atcccttctc gtcccaatg                                                19

<210> SEQ ID NO 10
<211> LENGTH: 23
<212> TYPE: DNA
<213> ORGANISM: Artificial Sequence
<220> FEATURE:
<223> OTHER INFORMATION: HV 2 -P146-50-52

<400> SEQUENCE: 10
ttcctgcctc atcctattat tta                                           23

<210> SEQ ID NO 11
<211> LENGTH: 16
<212> TYPE: DNA
<213> ORGANISM: Artificial Sequence
<220> FEATURE:
<223> OTHER INFORMATION: HV 2 -P263

<400> SEQUENCE: 11
acagccactt tccaca                                                   16

<210> SEQ ID NO 12
<211> LENGTH: 19
<212> TYPE: DNA
<213> ORGANISM: Artificial Sequence
<220> FEATURE:
<223> OTHER INFORMATION: HV 2 -P204-7

<400> SEQUENCE: 12
agtgtgttaa ttaattaat                                                19

<210> SEQ ID NO 13
<211> LENGTH: 19
<212> TYPE: DNA
<213> ORGANISM: Artificial Sequence
<220> FEATURE:
<223> OTHER INFORMATION: HV 2 -P235

<400> SEQUENCE: 13
gtaggacata ataataaca                                                19

<210> SEQ ID NO 14
<211> LENGTH: 13
<212> TYPE: DNA
<213> ORGANISM: Artificial Sequence
<220> FEATURE:
<223> OTHER INFORMATION: HV 2 -P249

<400> SEQUENCE: 14
attgaatgtc tgc                                                      13

```
<210> SEQ ID NO 15
<211> LENGTH: 17
<212> TYPE: DNA
<213> ORGANISM: Artificial Sequence
<220> FEATURE:
<223> OTHER INFORMATION: HV 2 -P195-9

<400> SEQUENCE: 15
gcgaacatac ttactaa                                                17

<210> SEQ ID NO 16
<211> LENGTH: 12
<212> TYPE: DNA
<213> ORGANISM: Artificial Sequence
<220> FEATURE:
<223> OTHER INFORMATION: HV 2 -P73

<400> SEQUENCE: 16
gggtatgcac gc                                                     12
```